United States Patent
Laine et al.

(10) Patent No.: US 7,498,440 B2
(45) Date of Patent: *Mar. 3, 2009

(54) MUSCARINIC ACETYLCHOLINE RECEPTOR ANTAGONISTS

(75) Inventors: Damane I. Laine, King of Prussia, PA (US); Michael R. Palovich, King of Prussia, PA (US); Brent W. McCleland, King of Prussia, PA (US); Christopher E. Neipp, King of Prussia, PA (US); Sonia M. Thomas, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/568,330

(22) PCT Filed: Apr. 27, 2005

(86) PCT No.: PCT/US2005/014386

§ 371 (c)(1), (2), (4) Date: May 3, 2007

(87) PCT Pub. No.: WO2005/104745

PCT Pub. Date: Nov. 10, 2005

(65) Prior Publication Data

US 2007/0185155 A1   Aug. 9, 2007

Related U.S. Application Data

(60) Provisional application No. 60/565,623, filed on Apr. 27, 2004.

(51) Int. Cl.
    C07D 453/02 (2006.01)
    A61K 31/44 (2006.01)
(52) U.S. Cl. ...................... 546/133; 514/305
(58) Field of Classification Search .................. 546/133; 514/305

See application file for complete search history.

(56) References Cited

U.S. PATENT DOCUMENTS

| | | | |
|---|---|---|---|
| 2,800,478 A | 7/1957 | Zirkle et al. | |
| 2,800,481 A | 7/1957 | Zirkle et al. | |
| 3,634,852 A | 1/1972 | Hartley et al. | |
| 5,590,645 A | 1/1997 | Davies et al. | |
| 5,780,466 A | 7/1998 | Emonds-Alt et al. | |
| 5,860,419 A | 1/1999 | Davies et al. | |
| 5,873,360 A | 2/1999 | Davies et al. | |
| 6,248,752 B1 | 6/2001 | Smith | |
| 6,262,066 B1 | 7/2001 | Tulshian et al. | |
| 6,350,758 B1 | 2/2002 | Kozikowski et al. | |
| 6,455,527 B2 | 9/2002 | Tulshian et al. | |
| 6,750,226 B2 | 6/2004 | Forner et al. | |
| 7,232,841 B2 | 6/2007 | Busch-Petersen et al. | |
| 7,276,521 B2 | 10/2007 | Busch-Petersen et al. | |
| 2005/0020660 A1 | 1/2005 | Guyaux et al. | |
| 2005/0113417 A1 | 5/2005 | Mammen et al. | |
| 2005/0209272 A1 | 9/2005 | Fernandez et al. | |
| 2005/0277676 A1 | 12/2005 | Laine et al. | |
| 2006/0160844 A1 | 7/2006 | Belmonte et al. | |
| 2006/0178395 A1 | 8/2006 | Belmonte et al. | |
| 2006/0178396 A1 | 8/2006 | Belmonte et al. | |
| 2007/0129396 A1 | 6/2007 | Wan et al. | |
| 2007/0135478 A1 | 6/2007 | Palovich et al. | |
| 2007/0149598 A1 | 6/2007 | Busch-Petersen et al. | |
| 2007/0173646 A1 | 7/2007 | Laine et al. | |
| 2007/0179180 A1 | 8/2007 | Busch-Petersen et al. | |
| 2007/0179184 A1 | 8/2007 | Busch-Petersen et al. | |
| 2007/0185088 A1 | 8/2007 | Busch-Petersen et al. | |
| 2007/0185090 A1 | 8/2007 | Busch-Petersen et al. | |
| 2007/0185148 A1 | 8/2007 | Busch-Petersen et al. | |
| 2007/0185155 A1 | 8/2007 | Laine et al. | |
| 2007/0232599 A1 | 10/2007 | Palovich et al. | |
| 2007/0249664 A1* | 10/2007 | Laine et al. ................. | 514/305 |

FOREIGN PATENT DOCUMENTS

| | | |
|---|---|---|
| EP | 0069715 | 6/1982 |
| GB | 2064336 | 6/1981 |
| GB | 2129691 | 5/1984 |
| GB | 2169265 | 7/1986 |
| GB | 2178965 | 2/1987 |
| GB | 2242134 | 9/1991 |
| WO | 87/05213 | 9/1987 |
| WO | 2004/012684 | 2/2004 |
| WO | 2006/050239 | 5/2006 |
| WO | 2006/055503 | 5/2006 |
| WO | 2006/055553 | 5/2006 |
| WO | 2006/062883 | 6/2006 |

(Continued)

OTHER PUBLICATIONS

Becker et al Helvetica Chimica Acta 1978, 61, 2596-2606.*

(Continued)

*Primary Examiner*—Rita J Desai
*Assistant Examiner*—John Mabry
(74) *Attorney, Agent, or Firm*—Dara L. Dinner; Theodore R. Furman; Charles M. Kinzig

(57) ABSTRACT

Muscarinic Acetylcholine Receptor Antagonists and methods of using them are provided.

49 Claims, No Drawings

FOREIGN PATENT DOCUMENTS

| WO | 2006/062931 | 6/2006 |
| WO | 2006/065755 | 6/2006 |
| WO | 2006/065788 | 6/2006 |
| WO | 2007/016639 | 2/2007 |
| WO | 2007/016650 | 2/2007 |
| WO | 2007/018508 | 2/2007 |
| WO | 2007/018514 | 2/2007 |
| WO | 2007/022351 | 2/2007 |

OTHER PUBLICATIONS

Ikeda, K et al., 2002, vol. 366, pp. 97-103, abstract, M3 receptor angagonism by the novel antimuscarinic agent solifenacin in the urinary bladder and salivary gland Naunyn-Schmiedeberg's Arch Pharmacol.
Caulfield (1993 *Pharmac. Ther.* 58:319-79).
Fryer and Jacoby (1998 *Am J Respir Crit Care Med* 158(5, pt 3) S 154-60).
Fryer et al. 1999 *Life Sci* 64 (6-7) 449-55.
Pauwels et al. 2001 *Am. J. Respir. Crit. Care Med.* 163:1256-1276.
U.S. Appl. No. 10/585,830, filed Jul. 12, 2006, Laine et al.
U.S. Appl. No. 10/598,743, filed Sep. 11, 2006, Budzik et al.
U.S. Appl. No. 10/598,750, filed Sep. 11, 2006, Jin et al.
U.S. Appl. No. 10/599,717, filed Oct. 6, 2006, Laine et al.
U.S. Appl. No. 11/570,981, filed Dec. 20, 2006, Cooper et al.
U.S. Appl. No. 11/573,097, filed Feb. 2, 2007, Busch-Petersen et al.
U.S. Appl. No. 11/573,099, filed Feb. 2, 2007, Busch-Petersen et al.
U.S. Appl. No. 11/766,318, filed Jun. 21, 2007, Busch-Petersen et al.
U.S. Appl. No. 11/766,371, filed Jun. 21, 2007, Busch-Petersen et al.
U.S. Appl. No. 11/774,885, filed May 1, 2006, Wan et al.
Brown, *History and Basic Properties*, Humana Press, USA pp. 7-9 (1989).
Costello, et al., *American Journal of Physiology*, vol. 276 (5) pp. L709-L714 (1999).
Hedge, et al., *Life Sciences*, vol. 64 (6/7) pp. 419-428 (1999).
Ikeda, et al., *Naunyn-Schmiedeberg's Arch Pharmacol.*, vol. 366, pp. 97-103, (2002).
Minette, et al., *Journal of Applied Physiology*, vol. 67(6) pp. 2461-2465 (1989).
Oprins, et al., *Annals of the New York Academy of Sciences*, vol. 915 pp. 102-106 (2000).
Ran, et al., *Yaoxue Xuebao*, vol. 19 (5) pp. 361-366 (1984) Abstract only.
Sarau, *Mol. Pharmacol.*, vol. 56 (3) p. 657-63 (1999).
Van Rossum, et al., *Arch. Int. Pharmacodyn.*, vol. 143 p. 299 (1963) Best Available Copy.
Wu, et al., *Zhongguo Yaowu Huazue Zazhi*, vol. 3 (1) pp. 23-26 (1993)Abstract only.
Zirkle, et al., *J Med Chem*, vol. 27 pp. 1269-1279 (1962).
Zirkle, et al., *J Med Chem*, vol. 27 pp. 1279-1285 (1962).
Zirkle, et al., *J Med Chem*, vol. 5 pp. 341-356 (1962).
Zhang, et al., *J Med Chem*, vol. 44 pp. 3937-3945 (2001).
Ran, et al., *Yaoxue Xuebao*, vol. 19 (5) pp. 361-366 (1984), with translation.
Wu, et al., *Zhongguo Yaowu Huaxue Zazhi*vol. 3(1) pp. 23-26 (1993), with translation.
Yu, et al., *Yaoxue Xuebao*, vol. 18(10) pp. 766-774 (1983), with translation.
Zhang, et al., *Yaoxue Xuebao*, vol. 20(10) pp. 752-758 (1985), with translation.

\* cited by examiner

MUSCARINIC ACETYLCHOLINE RECEPTOR ANTAGONISTS

This application is a 35 U.S.C. 371 application, which claims the benefit of U.S. Provisional Application No. 60/565,623, filed 27 Apr. 2004.

FIELD OF THE INVENTION

This invention relates to novel quinuclidines derivatives, pharmaceutical compositions, and use thereof in treating muscarinic acetylcholine receptor mediated diseases of the respiratory tract.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs where they mediate many of the vital functions. Muscarinic receptors can mediate both inhibitory and excitatory actions. For example, in smooth muscle found in the airways, $M_3$ mAChRs mediate contractile responses. For review, please see Caulfield (1993 *Pharmac. Ther.* 58:319-79).

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 *Am J Respir Crit Care Med* 158(5, pt 3) S 154-60).

Three subtypes of mAChRs have been identified as important in the lungs, $M_1$, $M_2$ and $M_3$ mAChRs. The $M_3$ mAChRs, located on airway smooth muscle, mediate muscle contraction. Stimulation of $M_3$ mAChRs activates the enzyme phospholipase C via binding of the stimulatory G protein Gq/11 (Gs), leading to liberation of phosphatidyl inositol-4,5-bisphosphate, resulting in phosphorylation of contractile proteins. $M_3$ mAChRs are also found on pulmonary submucosal glands. Stimulation of this population of $M_3$ mAChRs results in mucus secretion.

$M_2$ mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal $M_2$ mAChRs are located on postganglionic parasympathetic nerves. Under normal physiologic conditions, neuronal $M_2$ mAChRs provide tight control of acetylcholine release from parasympathetic nerves. Inhibitory $M_2$ mAChRs have also been demonstrated on sympathetic nerves in the lungs of some species. These receptors inhibit release of noradrenaline, thus decreasing sympathetic input to the lungs.

$M_1$ mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation (Fryer et al. 1999 *Life Sci* 64 (6-7) 449-55). This mAChR dysfunction results in airway hyperreactivity and hyperresponsiveness mediated by increased stimulation of $M_3$ mAChRs. Thus the identification of potent mAChR antagonists would be useful as therapeutics in these mAChR-mediated disease states.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 *Am. J Respir. Crit. Care Med.* 163:1256-1276).

Despite the large body of evidence supporting the use of anti-cholinergic therapy for the treatment of airway hyperreactive diseases, relatively few anti-cholinergic compounds are available for use in the clinic for pulmonary indications. More specifically, in United States, Ipratropium Bromide (Atrovent©; and Combivent©, in combination with albuterol) is currently the only inhaled anti-cholinergic marketed for the treatment of airway hyperreactive diseases. While this compound is a potent anti-muscarinic agent, it is short acting, and thus must be administered as many as four times daily in order to provide relief for the COPD patient. In Europe and Asia, the long-acting anti-cholinergic Tiotropium Bromide (Spiriva©) was recently approved, however this product is currently not available in the United States. Thus, there remains a need for novel compounds that are capable of causing blockade at mAChRs which are long acting and can be administered once-daily for the treatment of airway hyperreactive diseases such as asthma and COPD.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anti-cholinergic use.

SUMMARY OF THE INVENTION

This invention provides for a method of treating a muscarinic acetylcholine receptor (mAChR) mediated disease, wherein acetylcholine binds to an mAChR and which method comprises administering an effective amount of a compound of Formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

The present invention also provides for the novel compounds of Formula (I), and pharmaceutical compositions comprising a compound of Formula (I), and a pharmaceutical carrier or diluent.

Compounds of Formula (I) useful in the present invention are represented by the structure:

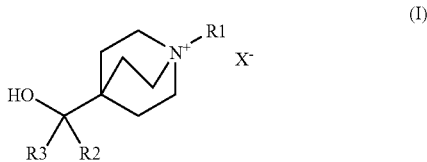
(I)

wherein:
R1 is selected from the group consisting of C1-15 alkyl, halosubstituted C1-15 alkyl, C1-15 alkyl cycloalkyl, cycloalkyl, C2-15 alkenyl, hydroxy substituted C1-15 alkyl, C1-15 alkyl aryl, C1-15 alkyl heteroaryl, (CR7R7)qNRaRa, (CR7R7)qNC(O)Ra, (CR7R7)qC(O)NRaRa, (CR7R7)qC(O)Ra, (CR7R7)qOC(O)Ra, (CR7R7)qNRaC(O)NRaRa, (CR7R7)qORc and (CR7R7)qNS(O)$_2$Ra R1 is selected from the group consisting of:

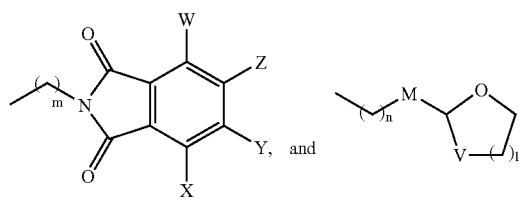

R1 is selected from the group consisting of:

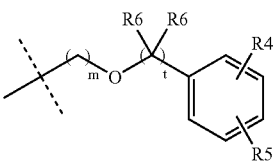

R2 and R3 are independently selected from the group consisting of aryl, C1-4 alkyl aryl, heteroaryl, C1-4 alkyl heteroaryl, heterocyclic and a C1-4 alkyl heterocyclic moiety, all of which moieties may be optionally substituted;

Ra is selected from the group consisting of hydrogen, C1-15 alkyl, C1-15 alkoxy, aryl, C1-15 alkyl aryl, heteroaryl, C1-15 alkyl heteroaryl, heterocyclic and a C1-15 alkyl heterocyclic moiety, all of which moieties may be optionally substituted;

Rc is selected from the group consisting of hydrogen, C1-15 alkyl, C1-15 alkoxy, heterocyclic and a C1-15 alkyl heterocyclic moiety, all of which moieties may be optionally substituted;

R4 and R5 are independently selected from the group consisting of hydrogen, halogen, C1-4 alkyl, aryl, C1-4 alkyl aryl, cyano, nitro, (CR7R7)pORb, (CR7R7)pNRbRb, or R4 and R5 together may form a 5 to 6 membered saturated or unsaturated ring; and wherein the alkyl, aryl, arylalkyl, heteroaryl, heteroalkyl, heterocyclic, heterocyclicalkyl groups may be optionally substituted;

R6 is selected from the group consisting of hydrogen, C1-4 alkyl;

q is 0 or an integer having a value of 1 to 15;
n is an integer having a value of 1 to 14;
m is an integer having a value of 1 to 15;
l is an integer having a value of 1 to 4;
t is 0 or an integer having a value of 1 to 5;
p is 0 or an integer having a value of 1 to 4;

X, Y, Z and W are independently selected from the group consisting of hydrogen, C1-4 alkyl;

V is selected from the group consisting of CH$_2$, O, S, and NRb;

M is O or CH$_2$;

Rb is selected from the group consisting of hydrogen, C1-4 alkyl, aryl and C1-4 alkyl aryl;

R7 is selected from the group consisting of hydrogen, C1-4 alkyl, halosubstituted C1-4 alkyl, and hydroxysubstituted C1-4 alkyl;

X— is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

DETAILED DESCRIPTION OF THE INVENTION

This invention related to novel bi-aryl 8-azoniabicyclo [3.2.1]octane compounds, pharmaceutical compositions, processes for their preparation, and use thereof in treating mAChR mediated diseases.

In a preferred embodiment of the present invention the compound is of formula (I) herein below:

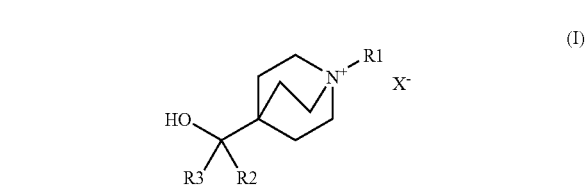
(I)

wherein:
R1 is selected from the group consisting of C1-10 alkyl, halosubstituted C1-10 alkyl, C1-10 alkyl aryl, C1-10 alkyl cycloalkyl, cycloalkyl, hydroxy substituted C1-10 alkyl, C2-10 alkenyl, (CR7R7)qORc; (CR7R7)qOC (O)Ra and (CR7R7)qNS(O)$_2$Ra;

or R1 is selected from the group consisting of:

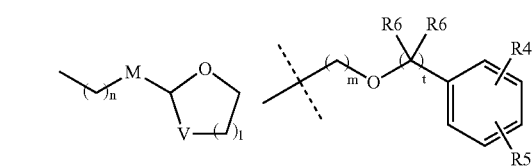

R2 and R3 are, independently, selected from the group consisting of:

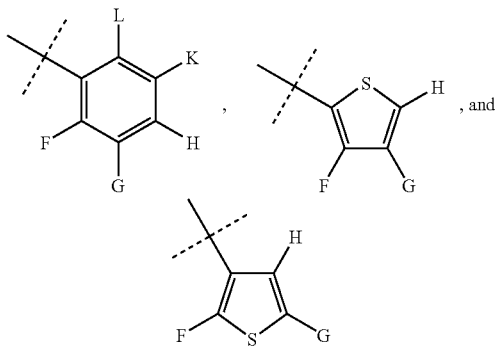

F, G, H, K and L are independently selected from the group consisting of hydrogen, halogen, C1-4 alkyl, halosubstituted C1-4 alkyl, hydoxysubstituted C1-4 alkyl, and C1-4 alkoxy;

Ra is selected from the group consisting of hydrogen, C1-10 alkyl, C1-10 alkoxy, aryl and heteroaryl, all of which moieties may be optionally substituted;

Rc is selected from the group consisting of hydrogen, C1-5 alkyl, C1-5 alkoxy, all of which moieties may be optionally substituted;

R4 and R5 are independently selected from the group consisting of hydrogen, halogen, C1-4 alkyl, aryl, C1-4 alkyl aryl, cyano, nitro, $(CR7R7)_pORb$, $(CR7R7)_pNRbRb$, or R4 and R5 together may form a 5 to 6 membered saturated or unsaturated ring;

q is 0 or an integer having a value of 1 to 5;
n is an integer having a value of 1 to 4;
m is an integer having a value of 1 to 5;
l is 1 or 2;
t is 0, 1 or 2;
p is 0, 1 or 2;
V is O, or $CH_2$;
R6 is selected from the group consisting of hydrogen, C1-4 alkyl;
M is O or $CH_2$;
Rb is selected from the group consisting of hydrogen, C1-4 alkyl, and aryl C1-4 alkyl
R7 is selected from the group consisting of hydrogen, and C1-4 alkyl;
X—is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

All of the aryl, heteroaryl, and heterocyclic containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)_{m'}C_{1-10}$ alkyl, wherein m' is 0, 1 or 2, such as methyl thio, methyl sulfinyl or methyl sulfonyl; amino, mono & di-substituted amino, such as in the $NR_{10}R_{11}$ group; $NHC(O)R_9$; $C(O)NR_{10}R_{11}$; $C(O)OH$; $S(O)_2NR_{10}R_{11}$; $NHS(O)_2R_9$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocyclicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl; $C_{1-10}$ alkoxy; $S(O)_{m'C1-10}$ alkyl; amino, mono & di-substituted alkyl amino, such as in the $NR_{10}R_{11}$ group; $C_{1-10}$ alkyl, or halosubstituted $C_{1-10}$ alkyl, such as $CF_3$.

The following terms, as used herein, refer to:

"halo"—all halogens, that is chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited to, pyrrole, pyrazole, furan, thiophene, quinoline, isoquinoline, quinazolinyl, pyridine, pyrimidine, oxazole, tetrazole, thiazole, thiadiazole, triazole, imidazole, indole or benzimidazole.

"heterocyclic" (on its own or in any combination, such as "heterocyclicalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S (O) of the corresponding sulfide, the term "thio" refers to the sulfide, and the term "sulfonyl" refers to the fully oxidized $S(O)_2$ moiety.

"wherein two $R_1$ moieties (or two Y moieties) may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Illustrative compounds of Formula (I) include:
1-(2-{[(3-fluorophenyl)methyl]oxy}ethyl)-4-[hydroxy (diphenyl)methyl]-1-azoniabicyclo[2.2.2]octane bromide 4-[hydroxy(diphenyl)methyl]-1-{2-[(phenylmethyl)oxy]
  ethyl}-1-azoniabicyclo[2.2.2]octane bromide
1-(2-{[(4-bromophenyl)methyl]oxy}ethyl)-4-[hydroxy
  (diphenyl)methyl]-1-azoniabicyclo[2.2.2]octane bromide
1-(2-{[(4-chlorophenyl)methyl]oxy}ethyl)-4-[hydroxy
  (diphenyl)methyl]-1-azoniabicyclo[2.2.2]octane bromide
4-[bis(4-fluorophenyl)(hydroxy)methyl]-1-{2-[(phenylm-
  ethyl)oxy]ethyl}-1-azoniabicyclo[2.2.2]octane bromide
4-{hydroxy[bis(3-methylphenyl)]methyl}-1-{2-[(phenylm-
  ethyl)oxy]ethyl}-1-azoniabicyclo[2.2.2]octane bromide
1-(2-{[(4-fluorophenyl)methyl]oxy}ethyl)-4-[hydroxy
  (diphenyl)methyl]-1-azoniabicyclo[2.2.2]octane bromide
4-[hydroxy(diphenyl)methyl]1-{2-[(phenylcarbonyl)oxy]
  ethyl}-1-azoniabicyclo[2.2.2]octane bromide
1-{3-[(3-fluorophenyl)oxy]propyl}-4-[hydroxy(diphenyl)
  methyl]-1-azoniabicyclo[2.2.2]octane bromide
4-{hydroxy[bis(4-methylphenyl)]methyl}-1-{2-[(phenylm-
  ethyl)oxy]ethyl}-1-azoniabicyclo[2.2.2]octane bromide
4-[hydroxy(diphenyl)methyl]-1-{3-[(methylsulfonyl)
  amino]propyl}-1-azoniabicyclo[2.2.2]octane bromide
4-[bis(3-fluorophenyl)(hydroxy)methyl]-1-{2-[(phenylm-
  ethyl)oxy]ethyl}-1-azoniabicyclo[2.2.2]octane bromide
1-{3-[(3-chlorophenyl)oxy]propyl}-4-[hydroxy(diphenyl)
  methyl]-1-azoniabicyclo[2.2.2]octane bromide
4-[hydroxy(di-2-thienyl)methyl]-1-[3-(phenyloxy)propyl]-
  1-azoniabicyclo[2.2.2]octane bromide
4-[hydroxy(diphenyl)methyl]-1-[3-(phenyloxy)propyl]-1-
  azoniabicyclo[2.2.2]octane bromide
1-(2-{[(4-cyanophenyl)methyl]oxy}ethyl)-4-[hydroxy
  (diphenyl)methyl]-1-azoniabicyclo[2.2.2]octane bromide
1-{3-[(4-bromophenyl)oxy]propyl}-4-[hydroxy(diphenyl)
  methyl]-1-azoniabicyclo[2.2.2]octane bromide
4-[bis(4-fluorophenyl)(hydroxy)methyl]-1-[3-(phenyloxy)
  propyl]-1-azoniabicyclo[2.2.2]octane bromide
1-{3-[(4-fluorophenyl)oxy]propyl}-4-[hydroxy(diphenyl)
  methyl]-1-azoniabicyclo[2.2.2]octane bromide
4-[hydroxy(diphenyl)methyl]-1-{2-[(1-methyl-1-phenyl-
  ethyl)oxy]ethyl}-1-azoniabicyclo[2.2.2]octane bromide
4-[hydroxy(diphenyl)methyl]-1-{2-[(2-naphthalenylmethyl)
  oxy]ethyl}-1-azoniabicyclo[2.2.2]octane bromide
4-[hydroxy(di-3-thienyl)methyl]-1-[3-(phenyloxy)propyl]-
  1-azoniabicyclo[2.2.2]octane bromide
4-[hydroxy(diphenyl)methyl]-1-[2-(phenyloxy)ethyl]-1-
  azoniabicyclo[2.2.2]octane bromide
4-{hydroxy[bis(3-methylphenyl)]methyl}-1-[3-(phenyloxy)
  propyl]-1-azoniabicyclo[2.2.2]octane bromide
4-{hydroxy[bis(4-methylphenyl)]methyl}-1-[3-(phenyloxy)
  propyl]-1-azoniabicyclo[2.2.2]octane bromide
4-[hydroxy(diphenyl)methyl]-1-(3-{[4-(methyloxy)phenyl]
  oxy}propyl)-1-azoniabicyclo[2.2.2]octane bromide
4-[hydroxy(diphenyl)methyl]-1-[3-(2-naphthalenyloxy)pro-
  pyl]-1-azoniabicyclo[2.2.2]octane bromide
4-[hydroxy(diphenyl)methyl]-1-[2-({[3-(methyloxy)phe-
  nyl]methyl}oxy)ethyl]-1-azoniabicyclo[2.2.2]octane bro-
  mide
4-[hydroxy(diphenyl)methyl]-1-(2-naphthalenylmethyl)-1-
  azoniabicyclo[2.2.2]octane bromide
4-[bis(3-fluorophenyl)(hydroxy)methyl]-1-[3-(phenyloxy)
  propyl]-1-azoniabicyclo[2.2.2]octane bromide
4-[hydroxy(di-2-thienyl)methyl]-1-[2-(phenyloxy)ethyl]-1-
  azoniabicyclo[2.2.2]octane bromide
4-(hydroxy{bis[3-(methyloxy)phenyl]}methyl)-1-{2-[(phe-
  nylmethyl)oxy]ethyl}-1-azoniabicyclo[2.2.2]octane bro-
  mide
4-[hydroxy(diphenyl)methyl]-1-{3-[(4-nitrophenyl)oxy]
  propyl}-1-azoniabicyclo[2.2.2]octane bromide
1-{3-[(2-fluorophenyl)oxy]propyl}-4-[hydroxy(diphenyl)
  methyl]-1-azoniabicyclo[2.2.2]octane bromide
4-[hydroxy(diphenyl)methyl]-1-{3-[(3-nitrophenyl)oxy]
  propyl}-1-azoniabicyclo[2.2.2]octane bromide
4-[hydroxy(diphenyl)methyl]-1-({3-[(trifluoromethyl)oxy]
  phenyl}methyl)-1-azoniabicyclo[2.2.2]octane bromide
4-[hydroxy(diphenyl)methyl]-1-[(5-nitro-2-furanyl)me-
  thyl]-1-azoniabicyclo[2.2.2]octane bromide
4-[hydroxy(diphenyl)methyl]-1-[2-(1H-indol-3-yl)ethyl]-1-
  azoniabicyclo[2.2.2]octane bromide
1-[3-(4-biphenylyloxy)propyl]-4-[hydroxy(diphenyl)me-
  thyl]-1-azoniabicyclo[2.2.2]octane bromide
4-[hydroxy(diphenyl)methyl]-1-{3-[(2-methylphenyl)oxy]
  propyl}-1-azoniabicyclo[2.2.2]octane bromide
4-[hydroxy(diphenyl)methyl]-1-(phenylmethyl)-1-azoniabi-
  cyclo[2.2.2]octane bromide
4-[hydroxy(diphenyl)methyl]-1-(2-{[2-(methyloxy)ethyl]
  oxy}ethyl)-1-azoniabicyclo[2.2.2]octane bromide
4-[hydroxy(diphenyl)methyl]-1-{3-[(phenylmethyl)oxy]
  propyl}-1-azoniabicyclo[2.2.2]octane bromide
4-[hydroxy(diphenyl)methyl]-1-[4-(phenyloxy)butyl]-1-
  azoniabicyclo[2.2.2]octane bromide
1-(1,3-dioxolan-2-ylmethyl)-4-[hydroxy(diphenyl)methyl]-
  1-azoniabicyclo[2.2.2]octane bromide
4-[hydroxy(diphenyl)methyl]-1-{3-[(2-hydroxyphenyl)oxy]
  propyl}-1-azoniabicyclo[2.2.2]octane bromide
1-hexyl-4-[hydroxy(diphenyl)methyl]-1-azoniabicyclo
  [2.2.2]octane bromide
4-[hydroxy(di-3-thienyl)methyl]-1-[2-(phenyloxy)ethyl]-1-
  azoniabicyclo[2.2.2]octane bromide
4-[hydroxy(diphenyl)methyl]-1-[3-({4-[(phenylmethyl)
  oxy]phenyl}oxy)propyl]-1-azoniabicyclo[2.2.2]octane
  bromide
1-[(3-bromophenyl)methyl]-4-[hydroxy(diphenyl)methyl]-
  1-azoniabicyclo[2.2.2]octane bromide
4-[hydroxy(di-2-naphthalenyl)methyl]-1-{2-[(phenylm-
  ethyl)oxy]ethyl}-1-azoniabicyclo[2.2.2]octane bromide
4-[hydroxy(diphenyl)methyl]-1-[2-(methyloxy)ethyl]-1-
  azoniabicyclo[2.2.2]octane bromide
4-(hydroxy{bis[4-(methyloxy)phenyl]}methyl)-1-{2-[(phe-
  nylmethyl)oxy]ethyl}-1-azoniabicyclo[2.2.2]octane bro-
  mide
1-{3-[(4-cyanophenyl)oxy]propyl}-4-[hydroxy(diphenyl)
  methyl]-1-azoniabicyclo[2.2.2]octane bromide
1-[2-(1-benzofuran-2-yl)-2-oxoethyl]-4-[hydroxy(diphenyl)
  methyl]-1-azoniabicyclo[2.2.2]octane bromide
1-[2-({[4-(1,1-dimethylethyl)phenyl]methyl}oxy)ethyl]-4-
  [hydroxy(diphenyl)methyl]-1-azoniabicyclo[2.2.2]octane
  bromide
4-[hydroxy(diphenyl)methyl]-1-{[3-(methyloxy)phenyl]
  methyl}-1-azoniabicyclo[2.2.2]octane bromide
4-[hydroxy(diphenyl)methyl]-1-({4-[(trifluoromethyl)oxy]
  phenyl}methyl)-1-azoniabicyclo[2.2.2]octane bromide
4-[hydroxy(diphenyl)methyl]-1-nonyl-1-azoniabicyclo
  [2.2.2]octane bromide
4-[hydroxy(di-2-naphthalenyl)methyl]-1-[3-(phenyloxy)
  propyl]-1-azoniabicyclo[2.2.2]octane bromide
1-[(4-fluorophenyl)methyl]-4-[hydroxy(diphenyl)methyl]-
  1-azoniabicyclo[2.2.2]octane bromide
1-[(4-bromophenyl)methyl]-4-[hydroxy(diphenyl)methyl]-
  1-azoniabicyclo[2.2.2]octane bromide
4-[hydroxy(diphenyl)methyl]-1-{[3-(trifluoromethyl)phe-
  nyl]methyl}-1-azoniabicyclo[2.2.2]octane bromide
1-[(2-fluorophenyl)methyl]-4-[hydroxy(diphenyl)methyl]-
  1-azoniabicyclo[2.2.2]octane bromide
4-[hydroxy(diphenyl)methyl]-1-{[4-(trifluoromethyl)phe-
  nyl]methyl}-1-azoniabicyclo[2.2.2]octane bromide 1-(5-hexen-1-yl)-4-[hydroxy(diphenyl)methyl]-1-azoniabicyclo[2.2.2]octane bromide
1-(3-cyclohexylpropyl)-4-[hydroxy(diphenyl)methyl]-1-azoniabicyclo[2.2.2]octane bromide
4-[hydroxy(diphenyl)methyl]-1-[2-(tetrahydro-2H-pyran-2-yloxy)ethyl]-1-azoniabicyclo[2.2.2]octane bromide
1-[2-(1,3-dioxo-1,3-dihydro-2H-isoindol-2-yl)ethyl]-4-[hydroxy(diphenyl)methyl]-1-azoniabicyclo[2.2.2]octane bromide
4-[hydroxy(diphenyl)methyl]-1-(2-phenylethyl)-1-azoniabicyclo[2.2.2]octane bromide
1-ethyl-4-[hydroxy(diphenyl)methyl]-1-azoniabicyclo[2.2.2]octane bromide
4-[hydroxy(diphenyl)methyl]-1-[(4-methylphenyl)methyl]-1-azoniabicyclo[2.2.2]octane bromide
1-butyl-4-[hydroxy(diphenyl)methyl]-1-azoniabicyclo[2.2.2]octane bromide
4-[hydroxy(diphenyl)methyl]-1-[2-(3-methyl-1H-pyrazol-1-yl)ethyl]-1-azoniabicyclo[2.2.2]octane bromide
4-(hydroxy{bis[4-(methyloxy)phenyl]}methyl)-1-[3-(phenyloxy)propyl]-1-azoniabicyclo[2.2.2]octane bromide
1-[3-(3-biphenylyloxy)propyl]-4-[hydroxy(diphenyl)methyl]-1-azoniabicyclo[2.2.2]octane bromide
4-[hydroxy(diphenyl)methyl]-1-[(1S)-1-methyl-2-oxo-2-(phenylamino)ethyl]-1-azoniabicyclo[2.2.2]octane bromide
4-[hydroxy(diphenyl)methyl]-1-propyl-1-azoniabicyclo[2.2.2]octane bromide
1-{3-[(2-bromophenyl)oxy]propyl}-4-[hydroxy(diphenyl)methyl]-1-azoniabicyclo[2.2.2]octane bromide
1-[(3-fluorophenyl)methyl]-4-[hydroxy(diphenyl)methyl]-1-azoniabicyclo[2.2.2]octane bromide
1-[(3,4-dichlorophenyl)methyl]-4-[hydroxy(diphenyl)methyl]-1-azoniabicyclo[2.2.2]octane bromide
1-[(2-fluoro-3-methylphenyl)methyl]-4-[hydroxy(diphenyl)methyl]-1-azoniabicyclo[2.2.2]octane bromide
4-[hydroxy(diphenyl)methyl]-1-{4-[(phenylmethyl)oxy]butyl}-1-azoniabicyclo[2.2.2]octane bromide
1-[(4-cyanophenyl)methyl]-4-[hydroxy(diphenyl)methyl]-1-azoniabicyclo[2.2.2]octane bromide
4-(hydroxy{bis[3-(methyloxy)phenyl]}methyl)-1-[3-(phenyloxy)propyl]-1-azoniabicyclo[2.2.2]octane bromide
1-(3-{[3-(diethylamino)phenyl]oxy}propyl)-4-[hydroxy(diphenyl)methyl]-1-azoniabicyclo[2.2.2]octane bromide
4-[hydroxy(diphenyl)methyl]-1-(2-propen-1-yl)-1-azoniabicyclo[2.2.2]octane bromide
1-{[4-(1,1-dimethylethyl)phenyl]methyl}-4-[hydroxy(diphenyl)methyl]-1-azoniabicyclo[2.2.2]octane bromide
4-[hydroxy(diphenyl)methyl]-1-(3-phenylpropyl)-1-azoniabicyclo[2.2.2]octane bromide
1-[(2,6-difluorophenyl)methyl]-4-[hydroxy(diphenyl)methyl]-1-azoniabicyclo[2.2.2]octane bromide
4-[hydroxy(diphenyl)methyl]-1-[2-({[2-(phenyloxy)-3-pyridinyl]carbonyl}amino)ethyl]-1-azoniabicyclo[2.2.2]octane bromide
4-[hydroxy(di-2-thienyl)methyl]-1-(2-phenylethyl)-1-azoniabicyclo[2.2.2]octane bromide
1-(3-bromopropyl)-4-[hydroxy(diphenyl)methyl]-1-azoniabicyclo[2.2.2]octane bromide
4-[hydroxy(diphenyl)methyl]-1-(2-hydroxyethyl)-1-azoniabicyclo[2.2.2]octane bromide
1-[(3-cyanophenyl)methyl]-4-[hydroxy(diphenyl)methyl]-1-azoniabicyclo[2.2.2]octane bromide
1-[2-({[(2,4-dichlorophenyl)amino]carbonyl}amino)ethyl]-4-[hydroxy(diphenyl)methyl]-1-azoniabicyclo[2.2.2]octane bromide
4-[hydroxy(diphenyl)methyl]-1-(4-penten-1-yl)-1-azoniabicyclo[2.2.2]octane bromide
1-{2-[(2,4-dibromophenyl)oxy]ethyl}-4-[hydroxy(diphenyl)methyl]-1-azoniabicyclo[2.2.2]octane bromide
1-[(2,4-difluorophenyl)methyl]-4-[hydroxy(diphenyl)methyl]1-azoniabicyclo[2.2.2]octane bromide
4-[hydroxy(diphenyl)methyl]-1-[3-(methyloxy)propyl]-1-azoniabicyclo[2.2.2]octane bromide
4-[hydroxy(diphenyl)methyl]-1-[3-({2-[(phenylmethyl)oxy]phenyl}oxy)propyl]-1-azoniabicyclo[2.2.2]octane bromide
[1-(2-aminoethyl)-1-azoniabicyclo[2.2.2]oct-4-yl](diphenyl)methanolate trifluoroacetate
4-[hydroxy(di-2-thienyl)methyl]-1-(3-phenylpropyl)-1-azoniabicyclo[2.2.2]octane bromide
4-[hydroxy(diphenyl)methyl]-1-methyl-1-azoniabicyclo[2.2.2]octane bromide
4-[hydroxy(diphenyl)methyl]-1-(tetrahydro-2H-pyran-2-ylmethyl)-1-azoniabicyclo[2.2.2]octane bromide
1-[(2,3-difluorophenyl)methyl]-4-[hydroxy(diphenyl)methyl]-1-azoniabicyclo[2.2.2]octane bromide
1-[2-(4-biphenylyl)-2-oxoethyl]-4-[hydroxy(diphenyl)methyl]-1-azoniabicyclo[2.2.2]octane bromide
4-[hydroxy(diphenyl)methyl]-1-[2-oxo-2-(4-pentylphenyl)ethyl]-1-azoniabicyclo[2.2.2]octane bromide
1-(2-{[(2,4-dichlorophenyl)carbonyl]amino}ethyl)-4-[hydroxy(diphenyl)methyl]-1-azoniabicyclo[2.2.2]octane bromide
4-[hydroxy(diphenyl)methyl]-1-(3-{[2-(methyloxy)phenyl]oxy}propyl)-1-azoniabicyclo[2.2.2]octane bromide
4-[hydroxy(diphenyl)methyl]-1-[(1-{[(phenylmethyl)oxy]carbonyl}-4-piperidinyl)methyl]-1-azoniabicyclo[2.2.2]octane bromide
4-[hydroxy(diphenyl)methyl]-1-[2-(2-naphthalenyl)-2-oxoethyl]-1-azoniabicyclo[2.2.2]octane bromide
4-[hydroxy(diphenyl)methyl]-1-[(4-nitrophenyl)methyl]-1-azoniabicyclo[2.2.2]octane bromide
1-butyl-4-[hydroxy(di-3-thienyl)methyl]-1-azoniabicyclo[2.2.2]octane bromide
4-[hydroxy(diphenyl)methyl]-1-(2-oxo-2-phenylethyl)-1-azoniabicyclo[2.2.2]octane bromide
1-[(3,4-difluorophenyl)methyl]-4-[hydroxy(diphenyl)methyl]-1-azoniabicyclo[2.2.2]octane bromide
1-(cyclopropylmethyl)-4-[hydroxy(diphenyl)methyl]-1-azoniabicyclo[2.2.2]octane bromide The preferred compounds useful in the present invention include:
1-(2-{[(3-fluorophenyl)methyl]oxy}ethyl)-4-[hydroxy(diphenyl)methyl]-1-azoniabicyclo[2.2.2]octane bromide
4-[hydroxy(diphenyl)methyl]1-{2-[(phenylmethyl)oxy]ethyl}-1-azoniabicyclo[2.2.2]octane bromide
1-(2-{[(4-bromophenyl)methyl]oxy}ethyl)-4-[hydroxy(diphenyl)methyl]-1-azoniabicyclo[2.2.2]octane bromide
1-(2-{[(4-chlorophenyl)methyl]oxy}ethyl)-4-[hydroxy(diphenyl)methyl]-1-azoniabicyclo[2.2.2]octane bromide
4-[bis(4-fluorophenyl)(hydroxy)methyl]-1-{2-[(phenylmethyl)oxy]ethyl}-1-azoniabicyclo[2.2.2]octane bromide
4-{hydroxy[bis(3-methylphenyl)]methyl}-1-{2-[(phenylmethyl)oxy]ethyl}-1-azoniabicyclo[2.2.2]octane bromide
1-(2-{[(4-fluorophenyl)methyl]oxy}ethyl)-4-[hydroxy(diphenyl)methyl]-1-azoniabicyclo[2.2.2]octane bromide
4-[hydroxy(diphenyl)methyl]-1-{2-[(phenylcarbonyl)oxy]ethyl}-1-azoniabicyclo[2.2.2]octane bromide
1-{3-[(3-fluorophenyl)oxy]propyl}-4-[hydroxy(diphenyl)methyl]-1-azoniabicyclo[2.2.2]octane bromide
4-{hydroxy[bis(4-methylphenyl)]methyl}-1-{2-[(phenylmethyl)oxy]ethyl}-1-azoniabicyclo[2.2.2]octane bromide 4-[hydroxy(diphenyl)methyl]-1-{3-[(methylsulfonyl)
  amino]propyl}-1-azoniabicyclo[2.2.2]octane bromide
4-[bis(3-fluorophenyl)(hydroxy)methyl]-1-{2-[(phenylm-
  ethyl)oxy]ethyl}-1-azoniabicyclo[2.2.2]octane bromide
1-{3-[(3-chlorophenyl)oxy]propyl}-4-[hydroxy(diphenyl)
  methyl]-1-azoniabicyclo[2.2.2]octane bromide
4-[hydroxy(di-2-thienyl)methyl]-1-[3-(phenyloxy)propyl]-
  1-azoniabicyclo[2.2.2]octane bromide
4-[hydroxy(diphenyl)methyl]-1-[3-(phenyloxy)propyl]-1-
  azoniabicyclo[2.2.2]octane bromide
1-(2-{[(4-cyanophenyl)methyl]oxy}ethyl)-4-[hydroxy
  (diphenyl)methyl]-1-azoniabicyclo[2.2.2]octane bromide
1-{3-[(4-bromophenyl)oxy]propyl}-4-[hydroxy(diphenyl)
  methyl]-1-azoniabicyclo[2.2.2]octane bromide
4-[bis(4-fluorophenyl)(hydroxy)methyl]-1-[3-(phenyloxy)
  propyl]-1-azoniabicyclo[2.2.2]octane bromide
1-{3-[(4-fluorophenyl)oxy]propyl}-4-[hydroxy(diphenyl)
  methyl]-1-azoniabicyclo[2.2.2]octane bromide
4-[hydroxy(diphenyl)methyl]-1-{2-[(1-methyl-1-phenyl-
  ethyl)oxy]ethyl}-1-azoniabicyclo[2.2.2]octane bromide
4-[hydroxy(diphenyl)methyl]-1-{2-[(2-naphthalenylmethyl)
  oxy]ethyl}-1-azoniabicyclo[2.2.2]octane bromide
4-[hydroxy(di-3-thienyl)methyl]-1-[3-(phenyloxy)propyl]-
  1-azoniabicyclo[2.2.2]octane bromide
4-[hydroxy(diphenyl)methyl]-1-[2-(phenyloxy)ethyl]-1-
  azoniabicyclo[2.2.2]octane bromide
4-{hydroxy[bis(3-methylphenyl)]methyl}-1-[3-(phenyloxy)
  propyl]-1-azoniabicyclo[2.2.2]octane bromide
4-{hydroxy[bis(4-methylphenyl)]methyl}-1-[3-(phenyloxy)
  propyl]-1-azoniabicyclo[2.2.2]octane bromide
4-[hydroxy(diphenyl)methyl]-1-(3-{[4-(methyloxy)phenyl]
  oxy}propyl)-1-azoniabicyclo[2.2.2]octane bromide
4-[hydroxy(diphenyl)methyl]-1-[3-(2-naphthalenyloxy)pro-
  pyl]-1-azoniabicyclo[2.2.2]octane bromide
4-[hydroxy(diphenyl)methyl]-1-[2-({[3-(methyloxy)phe-
  nyl]methyl}oxy)ethyl]-1-azoniabicyclo[2.2.2]octane bro-
  mide
4-[hydroxy(diphenyl)methyl]-1-(2-naphthalenylmethyl)-1-
  azoniabicyclo[2.2.2]octane bromide
4-[bis(3-fluorophenyl)(hydroxy)methyl]-1-[3-(phenyloxy)
  propyl]-1-azoniabicyclo[2.2.2]octane bromide
4-[hydroxy(di-2-thienyl)methyl]-1-[2-(phenyloxy)ethyl]-1-
  azoniabicyclo[2.2.2]octane bromide
4-(hydroxy{bis[3-(methyloxy)phenyl]}methyl)-1-{2-[(phe-
  nylmethyl)oxy]ethyl}-1-azoniabicyclo[2.2.2]octane bro-
  mide
4-[hydroxy(diphenyl)methyl]-1-{3-[(4-nitrophenyl)oxy]
  propyl}-1-azoniabicyclo[2.2.2]octane bromide
1-{3-[(2-fluorophenyl)oxy]propyl}-4-[hydroxy(diphenyl)
  methyl]-1-azoniabicyclo[2.2.2]octane bromide The more preferred compounds useful in the present invention include:

1-(2-{[(3-fluorophenyl)methyl]oxy}ethyl)-4-[hydroxy
  (diphenyl)methyl]-1-azoniabicyclo[2.2.2]octane bromide
4-[hydroxy(diphenyl)methyl]-1-{2-[(phenylmethyl)oxy]
  ethyl}-1-azoniabicyclo[2.2.2]octane bromide
1-(2-{[(4-bromophenyl)methyl]oxy}ethyl)-4-[hydroxy
  (diphenyl)methyl]-1-azoniabicyclo[2.2.2]octane bromide
1-(2-{[(4-chlorophenyl)methyl]oxy}ethyl)-4-[hydroxy
  (diphenyl)methyl]-1-azoniabicyclo[2.2.2]octane bromide
4-[bis(4-fluorophenyl)(hydroxy)methyl]-1-{2-[(phenylm-
  ethyl)oxy]ethyl}-1-azoniabicyclo[2.2.2]octane bromide
4-{hydroxy[bis(3-methylphenyl)]methyl}-1-{2-[(phenylm-
  ethyl)oxy]ethyl}-1-azoniabicyclo[2.2.2]octane bromide
1-(2-{[(4-fluorophenyl)methyl]oxy}ethyl)-4-[hydroxy
  (diphenyl)methyl]-1-azoniabicyclo[2.2.2]octane bromide
4-[hydroxy(diphenyl)methyl]-1-{2-[(phenylcarbonyl)oxy]
  ethyl}-1-azoniabicyclo[2.2.2]octane bromide
1-{3-[(3-fluorophenyl)oxy]propyl}-4-[hydroxy(diphenyl)
  methyl]-1-azoniabicyclo[2.2.2]octane bromide
4-{hydroxy[bis(4-methylphenyl)]methyl}-1-{2-[(phenylm-
  ethyl)oxy]ethyl}-1-azoniabicyclo[2.2.2]octane bromide
4-[hydroxy(diphenyl)methyl]-1-{3-[(methylsulfonyl)
  amino]propyl}-1-azoniabicyclo[2.2.2]octane bromide
4-[bis(3-fluorophenyl)(hydroxy)methyl]-1-{2-[(phenylm-
  ethyl)oxy]ethyl}-1-azoniabicyclo[2.2.2]octane bromide
1-{3-[(3-chlorophenyl)oxy]propyl}-4-[hydroxy(diphenyl)
  methyl]-1-azoniabicyclo[2.2.2]octane bromide
4-[hydroxy(di-2-thienyl)methyl]-1-[3-(phenyloxy)propyl]-
  1-azoniabicyclo[2.2.2]octane bromide
4-[hydroxy(diphenyl)methyl]-1-[3-(phenyloxy)propyl]-1-
  azoniabicyclo[2.2.2]octane bromide
1-(2-{[(4-cyanophenyl)methyl]oxy}ethyl)-4-[hydroxy
  (diphenyl)methyl]-1-azoniabicyclo[2.2.2]octane bromide
1-{3-[(4-bromophenyl)oxy]propyl}-4-[hydroxy(diphenyl)
  methyl]1-azoniabicyclo[2.2.2]octane bromide
4-[bis(4-fluorophenyl)(hydroxy)methyl]-1-[3-(phenyloxy)
  propyl]-1-azoniabicyclo[2.2.2]octane bromide
1-{3-[(4-fluorophenyl)oxy]propyl}-4-[hydroxy(diphenyl)
  methyl]-1-azoniabicyclo[2.2.2]octane bromide
4-[hydroxy(diphenyl)methyl]-1-{2-[(1-methyl-1-phenyl-
  ethyl)oxy]ethyl}-1-azoniabicyclo[2.2.2]octane bromide
4-[hydroxy(diphenyl)methyl]-1-{2-[(2-naphthalenylmethyl)
  oxy]ethyl}-1-azoniabicyclo[2.2.2]octane bromide
4-[hydroxy(di-3-thienyl)methyl]-1-[3-(phenyloxy)propyl]-
  1-azoniabicyclo[2.2.2]octane bromide
4-[hydroxy(diphenyl)methyl]-1-[2-(phenyloxy)ethyl]-1-
  azoniabicyclo[2.2.2]octane bromide
4-{hydroxy[bis(3-methylphenyl)]methyl}-1-[3-(phenyloxy)
  propyl]-1-azoniabicyclo[2.2.2]octane bromide The most preferred compounds useful in the present invention include:

1-(2-{[(3-fluorophenyl)methyl]oxy}ethyl)-4-[hydroxy
  (diphenyl)methyl]-1-azoniabicyclo[2.2.2]octane bromide
4-[hydroxy(diphenyl)methyl]-1-{2-[(phenylmethyl)oxy]
  ethyl}-1-azoniabicyclo[2.2.2]octane bromide
1-(2-{[(4-bromophenyl)methyl]oxy}ethyl)-4-[hydroxy
  (diphenyl)methyl]-1-azoniabicyclo[2.2.2]octane bromide
1-(2-{[(4-chlorophenyl)methyl]oxy}ethyl)-4-[hydroxy
  (diphenyl)methyl]-1-azoniabicyclo[2.2.2]octane bromide
4-[bis(4-fluorophenyl)(hydroxy)methyl]-1-{2-[(phenylm-
  ethyl)oxy]ethyl}-1-azoniabicyclo[2.2.2]octane bromide
4-{hydroxy[bis(3-methylphenyl)]methyl}-1-{2-[(phenylm-
  ethyl)oxy]ethyl}-1-azoniabicyclo[2.2.2]octane bromide
1-(2-{[(4-fluorophenyl)methyl]oxy}ethyl)-4-[hydroxy
  (diphenyl)methyl]-1-azoniabicyclo[2.2.2]octane bromide
4-[hydroxy(diphenyl)methyl]-1-{2-[(phenylcarbonyl)oxy]
  ethyl}-1-azoniabicyclo[2.2.2]octane bromide

METHODS OF PREPARATION

The compounds of Formula (I) may be obtained by applying synthetic procedures, some of which are illustrated in the Schemes below. The synthesis provided in this Scheme is applicable for producing compounds of Formula (I) having a variety of different R1, R2 and R3 groups which are reacted, employing substituents which are suitably protected, to achieve compatibility with the reactions outlined herein. Subsequent deprotection, in those cases, then affords compounds of the nature generally disclosed. While the Schemes are shown with compounds only of Formula (I), this is merely for illustration purpose only.

As shown in Scheme 1, the desired compounds of Formula (I) can be prepared in four synthetic steps from the commercially available ethyl 4-piperidinecarboxylate precursor 1. Compound 1 is reacted with 1-bromo-2-chloroethane following standard alkylation procedures well known in the art such as potassium carbonate in acetone followed by reaction of the intermediate with lithium diisopropylamide in an aprotic solvent such as tetrahydrofurann to give the quinuclidine intermediate 2. Condensation of compound 2 with organometallic reagents such as a Grignard reagent or an organolithium derivative in an aprotic solvent such as tetrahydrofuran, results in the formation of the tertiary alcohol 3 of Formula (I) (R1=nothing). Further N-alkylation of compound 3 with a suitable alkyl halide in a organic solvent such as chloroform or acetontirile gives compound 4 of Formula (I) (R1 not nothing).

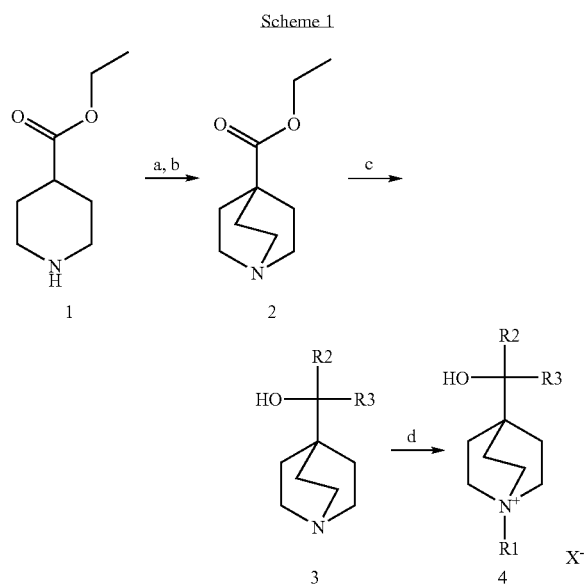

Scheme 1

Reagents and conditions: a) 1-bromo-2-chloroethane, K$_2$CO$_3$, acetone; b) LDA, THF; c) R$_2$M then R$_3$M, THF; d) R1X, ACN, CHCl$_3$.

SYNTHETIC EXAMPLES

The invention will now be described by reference to the following Examples which are merely illustrative and are not to be construed as a limitation of the scope of the present invention. All temperatures are given in ° C. Thin layer chromatography (t.l.c.) was carried out on silica and column chromatography on silica (Flash column chromatography using Merck 9385 unless stated otherwise).

The following are the experimental conditions for the LC-MS.

LC-MS Experimental Conditions:
Liquid Chromatograph:
System: Shimadzu LC system with SCL-10A Controller and dual UV detector
Autosampler: Leap CTC with a Valco six port injector
Column: Aquasil/Aquasil (C18 40×1 mm)
Inj. Volume (µL): 2.0
Solvent A: H$_2$O, 0.02% TFA
Solvent B: MeCN, 0.018% TFA
Gradient: linear Channel A: UV 214 nm
Channel B: ELS

| Step | Time (min) | Dura. (min) | Flow (µL/min) | Sol. A | Sol. B |
|---|---|---|---|---|---|
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

Mass Spectrometer: PE Sciex Single Quadrupole LC/MS API-150
Polarity: Positive
Acquisition mode: Profile
The preparatory HPLC was conducted using a Gilson HPLC system under the following conditions:
Column: 75×33 mm I. D., S-5 um, 12 nm
Flow rate: 30 mL/min
Injection Volume: 0.800 mL
Room temperature
Solvent A: water
Solvent B: acetonitrile
All solvents used herein are of the highest available purity and all reactions are run under anhydrous conditions under an air atmosphere unless otherwise indicated.

Example 1

Preparation of 1-azabicyclo[2.2.2]oct-4-yl(diphenyl)methanol

Ethyl 1-(2-chloroethyl)-4-piperidinecarboxylate

To a solution of ethyl nipecotate (20.0 mL, 130 mmol) in acetone (180 mL) was added 1-bromo-2-chloroethane (21.6 mL, 260 mmol) followed by anhydrous K$_2$CO$_3$ (27.12 g, 196 mmol). The reaction mixture was stirred for 24 h and then concentrated under vacuum. The resulting residue was treated with H$_2$O (75 mL) and extracted with Et$_2$O. The combined organic layers were dried with MgSO$_4$, filtered, and concentrated under vacuum. Purification of the crude residue by flash chromatography (50% Et$_2$O/50% hexane) on silica gel gave the title compound (10.99 g, 38.6%). EI-MS m/z 220(M+H$^+$) Rt (1.20 min).

Ethyl 1-azabicyclo[2.2.2]octane-4-carboxylate

A solution of ethyl 1-(2-chloroethyl)-4-piperidinecarboxylate (20.42 g, 92.9 mmol) in THF (600 mL) was cooled to −50° C. under Ar. LDA (2.0 M in heptane/THF/ethyl benzene, 70 mL, 140 mmol) was slowly added to the solution at −50° C. over 25 min. The reaction was allowed to warm up to room temperature over 16 h. The reaction was quenched with K$_2$CO$_3$ (saturated aqueous) (500 mL) and extracted with Et$_2$O (3×500 mL). The combined organic layers were dried over MgSO$_4$, filtered, and concentrated under vacuum. The resulting orange oil was co-evaporated three times with DCM to remove excess ethyl benzene, resulting in the title compound (16.29 g, 95.7%). EI-MS m/z 184(M+H$^+$) Rt (1.08 min).

1-Azabicyclo[2.2.2]oct-4-yl(diphenyl)methanol

A solution of phenyllithium (1.5-1.7 M in 70 cyclohexane/30 ether, 20.0 mL, 32 mmol) was chilled down to −30° C.

under Ar. Ethyl 1-azabicyclo[2.2.2]octane-4-carboxylate (1.51 g, 8.23 mmol) in THF (20 mL) was slowly added to the reaction mixture at −30° C. over 25 min. The reaction was allowed to warm up to room temperature over 16 h. The reaction was quenched with $H_2O$ and then evaporated to dryness under vacuum. $H_2O$ and EtOAc were added, causing a white solid to crash out. This solid was filtered off, to give the title compound (0.79 g). The aqueous phase was further extracted with EtOAc, the combined organic layers were dried over $MgSO_4$, filtered, and concentrated under vacuum. The crude product was treated with EtOAc and hexane and filtered to yield more of the title compound (0.67 g). Total yield (1.46 g, 60.7%). EI-MS m/z 294(M+H$^+$) Rt (1.37 min).

Example 2

Preparation of 4-[hydroxy(diphenyl)methyl]-1-(2-phenylethyl)-1-azoniabicyclo[2.2.2]octane bromide To a solution of 1-azabicyclo[2.2.2]oct-4-yl(diphenyl)methanol (0.0775 g, 0.264 mmol) in $CH_3CN$/DCM/MeOH (2 mL/2 mL/1 mL) was added (2-bromoethyl)benzene (0.38 mL, 2.78 mmol). The solution was allowed to stir at room temperature for 4 days and then concentrated under vacuum to give a white solid. This residue was dissolved in DMSO and purified by preparatory HPLC to give the title compound (0.0612 g, 48.6%). EI-MS m/z 398(M$^+$) Rt (2.06 min).

Example 3

Preparation of 4-[hydroxy(diphenyl)methyl]-1-[2-(phenyloxy)ethyl]-1-azoniabicyclo[2.2.2]octane bromide General Procedure for Salt Formation without HPLC Purification.

To a solution of 1-azabicyclo[2.2.2]oct-4-yl(diphenyl)methanol (0.055 0 g, 0.187 mmol) in 2 $CH_3CN$/3 $CHCl_3$ (2.5 mL) was added 2-bromoethyl phenyl ether (0.06 0 g, 0.29 mmol). The solution was stirred at 60° C. for 16 h. The reaction was cooled down to room temperature and then diluted with ethyl acetate and hexane causing a solid to crash out of solution. This solid was filtered off, and washed with hexane to give the title compound (0.063 g, 67.6%). EI-MS m/z 414(M$^+$) Rt (1.94 min).

Example 4

Preparation of 1-(cyclopropylmethyl)-4-[hydroxy(diphenyl)methyl]-1-azoniabicyclo[2.2.2]octane bromide General Procedure for Salt Formation with HPLC Purification.

To a solution of 1-azabicyclo[2.2.2]oct-4-yl(diphenyl)methanol (0.0552 g, 0.188 mmol) in 2 $CH_3CN$/3 $CHCl_3$ (2.5 mL) was added (bromomethyl) cyclopropane (0.025 mL, 0.257 mmol). The solution was heated at 60° C. for 16 h, cooled down to room temperature and the solvents evaporated under vacuum. The residue was taken up in 2.5 mL of DMSO and purified by preparatory HPLC (without TFA) to give the title compound (0.031 9 g, 39.9%). EI-MS m/z 348(M$^+$) Rt (1.69 min).

Example 5

Preparation of 4-[hydroxy(diphenyl)methyl]-1-(2-oxo-2-phenylethyl)-1-azoniabicyclo[2.2.2]octane bromide Following the general procedure outlined in Example 4, 1-azabicyclo[2.2.2]oct-4-yl(diphenyl)methanol (0.0567 g, 0.193 mmol) and 2-bromo-1-phenylethanone (0.0487 g, 0.245 mmol) in 2 $CH_3CN$/3 $CHCl_3$ (2.5 mL) were reacted to give the desired product (0.0410 g, 43.0%). EI-MS m/z 412 (M$^+$) Rt (1.90 min).

Example 6

Preparation of 4-[hydroxy(diphenyl)methyl]-1-[3-(phenyloxy)propyl]-1-azoniabicyclo[2.2.2]octane bromide Following the general procedure outlined in Example 3, 1-azabicyclo[2.2.2]oct-4-yl(diphenyl)methanol (0.045 g, 0.153 mmol) and 3-bromopropyl phenyl ether (0.035 mL, 0.222 mmol) in 2 $CH_3CN$/3 $CHCl_3$ (3.0 mL) were reacted to give the desired product (0.0662 g, 86.0%). EI-MS m/z 428 (M$^+$) Rt (1.97 min).

Example 7

Preparation of 4-[hydroxy(diphenyl)methyl]-1-[4-(phenyloxy)butyl]-1-azoniabicyclo[2.2.2]octane bromide Following the general procedure outlined in Example 4, 1-azabicyclo[2.2.2]oct-4-yl(diphenyl)methanol (0.0604 g, 0.206 mmol) and 4-bromobutyl phenyl ether (0.106 g, 0.463 mmol) in 2 $CH_3CN$/3 $CHCl_3$ (5.0 mL) were reacted to give the desired product (0.0649 g, 64.9%). EI-MS m/z 442(M$^+$) Rt (2.13 min).

Example 8

Preparation of 4-[hydroxy(diphenyl)methyl]-1-[2-(tetrahydro-2H-pyran-2-yloxy)ethyl]-1-azoniabicyclo[2.2.2]octane bromide Following the general procedure outlined in Example 4, 1-azabicyclo[2.2.2]oct-4-yl(diphenyl)methanol (0.0696 g, 0.237 mmol) and 2-[(2-bromoethyl)oxy]tetrahydro-2H-pyran (0.080 mL, 0.529 mmol) in 2 $CH_3CN$/3 $CHCl_3$ (5.0 mL) were reacted to give the desired product (0.0348 g, 31.6%). EI-MS m/z 422(M$^+$) Rt (1.85 min).

Example 9

Preparation of 4-[hydroxy(diphenyl)methyl]-1-{4-[(phenylmethyl)oxy]butyl}-1-azoniabicyclo[2.2.2]octane bromide Following the general procedure outlined in Example 4, 1-azabicyclo[2.2.2]oct-4-yl(diphenyl)methanol (0.0646 g, 0.220 mmol) and 4-bromobutyl phenylmethyl ether (0.090 mL, 0.472 mmol) in 2 $CH_3CN$/3 $CHCl_3$ (5.0 mL) were reacted to give the desired product (0.0531 g, 48.3%). EI-MS m/z 456(M$^+$) Rt (2.09 min).

Example 10

Preparation of 4-[hydroxy(diphenyl)methyl]-1-{3-[(phenylmethyl)oxy]propyl}-1-azoniabicyclo[2.2.2]octane bromide Following the general procedure outlined in Example 4, 1-azabicyclo[2.2.2]oct-4-yl(diphenyl)methanol (0.0677 g, 0.231 mmol) and 3-bromopropyl phenylmethyl ether (0.070 mL, 0.396 mmol) in 2 $CH_3CN$/3 $CHCl_3$ (4.0 mL) were reacted to give the desired product (0.0663 g, 55.2%). EI-MS m/z 442($M^+$) Rt (2.23 min).

Example 11

Preparation of 1-{2-[(2,4-dibromophenyl)oxy]ethyl}-4-[hydroxy(diphenyl)methyl]-1-azoniabicyclo[2.2.2]octane bromide Following the general procedure outlined in Example 4, 1-azabicyclo[2.2.2]oct-4-yl(diphenyl)methanol (0.0557 g, 0.190 mmol) and 2-bromoethyl 2,4-dibromophenyl ether (0.110 g, 0.306 mmol) in 2 $CH_3CN$/3 $CHCl_3$ (4.0 mL) were reacted to give the desired product (0.0525 g, 43.8%). EI-MS m/z 572($M^+$) Rt (2.26 min).

Example 12

Preparation of 1-(3-bromopropyl)-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0979 g, 0.334 mmol) and 1,3-dibromopropane (0.35 mL, 3.448 mmol) in 2 $CH_3CN$/3 $CHCl_3$ (15.0 mL) were reacted to give the desired product (0.0712 g, 43.1%). EI-MS m/z 415($M^+$) Rt (1.79 min).

Example 13

Preparation of 4-[hydroxy(diphenyl)methyl]-1-(tetrahydro-2H-pyran-2-ylmethyl)-1-azoniabicyclo[2.2.2]octane bromide Following the general procedure outlined in Example 4, 1-azabicyclo[2.2.2]oct-4-yl(diphenyl)methanol (0.0677 g, 0.231 mmol) and 3-(bromomethyl)tetrahydro-2H-pyran (0.050 mL, 0.390 mmol) in 2 $CH_3CN$/3 $CHCl_3$ (4.0 mL) were reacted to give the desired product (0.0508 g, 50.8%). EI-MS m/z 392($M^+$) Rt (1.84 min).

Example 14

Preparation of 1-(1,3-dioxolan-2-ylmethyl)-4-[hydroxy(diphenyl)methyl]-1-azoniabicyclo[2.2.2]octane bromide Following the general procedure outlined in Example 4, 1-azabicyclo[2.2.2]oct-4-yl(diphenyl)methanol (0.0574 g, 0.196 mmol) and 2-(bromomethyl)-1,3-dioxolane (0.040 mL, 0.386 mmol) in 2 $CH_3CN$/3 $CHCl_3$ (4.0 mL) were reacted to give the desired product (0.0112 g, 12.4%). EI-MS m/z 380($M^+$) Rt (1.64 min).

Example 15

Preparation of 1-ethyl-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0581 g, 0.198 mmol) and bromoethane (0.030 mL, 0.402 mmol) in 2 $CH_3CN$/3 $CHCl_3$ (4.0 mL) were reacted to give the desired product (0.0434 g, 54.9%). EI-MS m/z 322($M^+$) Rt (1.56 min).

Example 16

Preparation of 4-[hydroxy(diphenyl)methyl]-1-nonyl-1-azoniabicyclo[2.2.2]octane bromide Following the general procedure outlined in Example 4, 1-azabicyclo[2.2.2]oct-4-yl(diphenyl)methanol (0.0561 g, 0.191 mmol) and 1-bromononane (0.055 mL, 0.288 mmol) in 2 $CH_3CN$/3 $CHCl_3$ (4.0 mL) were reacted to give the desired product (0.0435 g, 45.8%). EI-MS m/z 420($M^+$) Rt (2.34 min).

Example 17

Preparation of 4-[hydroxy(diphenyl)methyl]-1-(4-penten-1-yl)-1-azoniabicyclo[2.2.2]octane bromide Following the general procedure outlined in Example 3, 1-azabicyclo[2.2.2]oct-4-yl(diphenyl)methanol (0.0608 g, 0.207 mmol) and 5-bromo-1-pentene (0.045 mL, 0.380 mmol) in 2 $CH_3CN$/3 $CHCl_3$ (4.0 mL) were reacted to give the desired product (0.0806 g, 88.6%). EI-MS m/z 362($M^+$) Rt (1.88 min).

Example 18

Preparation of 4-[hydroxy(diphenyl)methyl]-1-(2-hydroxyethyl)-1-azoniabicyclo[2.2.2]octane bromide Following the general procedure outlined in Example 3, 1-azabicyclo[2.2.2]oct-4-yl(diphenyl)methanol (0.0638 g, 0.217 mmol) and 2-bromoethanol (0.035 mL, 0.494 mmol) in 2 $CH_3CN$/3 $CHCl_3$ (4.0 mL) were reacted to give the desired product (0.0541 g, 60.1%). EI-MS m/z 338($M^+$) Rt (1.42 min).

Example 19

Preparation of 1-(5-hexen-1-yl)-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0637 g, 0.217 mmol) and 6-bromo-1-hexene (0.050 mL, 0.373 mmol) in 2 $CH_3CN$/3 $CHCl_3$ (5.0 mL) were reacted to give the desired product (0.0664 g, 67.1%). EI-MS m/z 376($M^+$) Rt (1.90 min).

Example 20

Preparation of 4-[hydroxy(diphenyl)methyl]-1-methyl-1-azoniabicyclo[2.2.2]octane bromide Following the general procedure outlined in Example 3, 1-azabicyclo[2.2.2]oct-4-yl(diphenyl)methanol (0.0638 g, 0.217 mmol) and bromomethane (2.0 M in t-Butylmethyl ether, 0.250 mL, 0.500 mmol) in 2 CH$_3$CN/3 CHCl$_3$ (4.0 mL) were reacted to give the desired product (0.0739 g, 88.0%). EI-MS m/z 308(M$^+$) Rt (1.58 min).

Example 21

Preparation of 4-[hydroxy(diphenyl)methyl]-1-[2-(methyloxy)ethyl]-1-azoniabicyclo[2.2.2]octane bromide Following the general procedure outlined in Example 4, 1-azabicyclo[2.2.2]oct-4-yl(diphenyl)methanol (0.0597 g, 0.203 mmol) and 2-bromoethyl methyl ether (0.030 mL, 0.319 mmol) in 2 CH$_3$CN/3 CHCl$_3$ (4.0 mL) were reacted to give the desired product (0.0372 g, 42.8%). EI-MS m/z 352 (M$^+$) Rt (1.69 min).

Example 22

Preparation of 1-[2-(1,3-dioxo-1,3-dihydro-2H-isoindol-2-yl)ethyl]-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0916 g, 0.312 mmol) and 2-(2-bromoethyl)-1H-isoindole-1,3(2H)-dione (0.130 g, 0.512 mmol) in 2 CH$_3$CN/3 CHCl$_3$ (4.0 mL) were reacted give the desired product (0.0881 g, 51.8%). EI-MS m/z 467(M$^+$) Rt (1.91 min).

Example 23

Preparation of 1-[3-(1,3-dioxo-1,3-dihydro-2H-isoindol-2-yl)propyl]-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0861 g, 0.293 mmol) and 2-(3-bromopropyl)-1H-isoindole-1,3(2H)-dione (0.118 g, 0.440 mmol) in 2 CH$_3$CN/3 CHCl$_3$ (5.0 mL) were reacted to give the desired product (0.1319 g, 82.4%). EI-MS m/z 481(M$^+$) Rt (1.90 min).

Example 24

Preparation of 4-[hydroxy(diphenyl)methyl]-1-(3-phenylpropyl)-1-azoniabicyclo[2.2.2]octane bromide Following the general procedure outlined in Example 3, 1-azabicyclo[2.2.2]oct-4-yl(diphenyl)methanol (0.0625 g, 0.213 mmol) and (3-bromopropyl)benzene (0.050 mL, 0.329 mmol) in 2 CH$_3$CN/3 CHCl$_3$ (5.0 mL) were reacted to give the desired product (0.0722 g, 72.2%). EI-MS m/z 412(M$^+$) Rt (2.01 min).

Example 25

Preparation of 4-[hydroxy(diphenyl)methyl]-1-(2-{[2-(methyloxy)ethyl]oxy}ethyl)-1-azoniabicyclo[2.2.2]octane bromide Following the general procedure outlined in Example 3, 1-azabicyclo[2.2.2]oct-4-yl(diphenyl)methanol (0.0665 g, 0.227 mmol) and 1-bromo-2-{[2-(methyloxy)ethyl]oxy}ethane (0.05 5 mL, 0.405 mmol) in 2 CH$_3$CN/3 CHCl$_3$ (4.0 mL) were reacted to give the desired product (0.0843 g, 78.8%). EI-MS m/z 396(M$^+$) Rt (1.64 min).

Example 26

Preparation of 1-[4-(ethyloxy)-4-oxobutyl]-4-[hydroxy(diphenyl)methyl]-1-azoniabicyclo[2.2.2]octane bromide Following the general procedure outlined in Example 4, 1-azabicyclo[2.2.2]oct-4-yl(diphenyl)methanol (0.0679 g, 0.231 mmol) and ethyl 4-bromobutanoate (0.055 mL, 0.524 mmol) in 2 CH$_3$CN/3 CHCl$_3$ (4.0 mL) were reacted to give the desired product (0.0637 g, 57.9%). EI-MS m/z 408(M$^+$) Rt (1.80 min).

Example 27

Preparation of 1-azabicyclo[2.2.2]oct-4-yl(di-2-thienyl)methanol

A solution of 2-thienyllithium (1.0M in THF, 9.10 mL, 9.10 mmol) was chilled down to −30° C. under Ar. Ethyl 1-azabicyclo[2.2.2]octane-4-carboxylate (0.4196 g, 2.289 mmol) in THF (8 mL) was slowly added to the reaction mixture over 20 min. The reaction was allowed to warm up to room temperature over 16 h. The reaction was quenched with water and then evaporated to dryness. H$_2$O and DCM were added, causing a light brown solid to crash out. This solid was filtered off to give the title compound (0.4161 g, 59.5%). EI-MS m/z 306(M+H$^+$) Rt (1.35 min).

Example 28

Preparation of 4-[hydroxy(di-2-thienyl)methyl]-1-[2-(phenyloxy)ethyl]-1-azoniabicyclo[2.2.2]octane bromide Following the general procedure outlined in Example 4, 1-azabicyclo[2.2.2]oct-4-yl(di-2-thienyl)methanol (0.0693 g, 0.227 mmol) and 2-bromoethyl phenyl ether (0.056 g, 0.279 mmol) in 1 MeOH/1 CHCl$_3$ (3.0 mL) were reacted to give the desired product (0.0822 g, 74.7%). EI-MS m/z 426 (M$^+$) Rt (2.00 min).

Example 29

Preparation of 4-[hydroxy(di-2-thienyl)methyl]-1-[3-(phenyloxy)propyl]-1-azoniabicyclo[2.2.2]octane bromide Following the general procedure outlined in Example 4, 1-azabicyclo[2.2.2]oct-4-yl(di-2-thienyl)methanol (0.0578 g, 0.189 mmol) and 3-bromopropyl phenyl ether (0.033 mL, 0.209 mmol) in 1 MeOH/1 CHCl$_3$ (4.0 mL) were reacted to give the desired product (0.0448 g, 45.4%). EI-MS m/z 440 (M$^+$) Rt (1.94 min).

Example 30

Preparation of 4-[hydroxy(di-2-thienyl)methyl]-1-(2-phenylethyl)-1-azoniabicyclo[2.2.2]octane bromide Following the general procedure outlined in Example 4, 1-azabicyclo[2.2.2]oct-4-yl(di-2-thienyl)methanol (0.0658 g, 0.215 mmol) and (2-bromoethyl)benzene (0.050 mL, 0.366 mmol) in 1 MeOH/1 CHCl$_3$ (4.0 mL) were reacted to give the desired product (0.051 4 g, 48.9%). EI-MS m/z 410(M$^+$) Rt (1.83 min).

Example 31

Preparation of 4-[hydroxy(di-2-thienyl)methyl]-1-(3-phenylpropyl)-1-azoniabicyclo[2.2.2]octane bromide Following the general procedure outlined in Example 4, 1-azabicyclo[2.2.2]oct-4-yl(di-2-thienyl)methanol (0.0688 g, 0.225 mmol) and (3-bromopropyl)benzene (0.070 mL, 0.460 mmol) in 1 MeOH/1 CHCl$_3$ (4.0 mL) were reacted to give the desired product (0.0685 g, 62.3%). EI-MS m/z 424 (M$^+$) Rt (1.97 min).

Example 32

Preparation of 1-butyl-4-[hydroxy(di-3-thienyl)methyl]-1-azoniabicyclo[2.2.2]octane bromide A solution of n-Butyl lithium (2.5M in hexanes, 5.0 mL, 12.5 mmol) was chilled to −78° C. under Ar. 3-Bromothiophene (1.15 mL, 12.3 mmol) dissolved in ethyl ether (4.0 mL) was slowly added to the reaction mixture. The reaction was stirred for 30 min and then ethyl 1-azabicyclo[2.2.2]octane-4-carboxylate (0.7640 g, 4.16 mmol) in THF/Et$_2$O (4 mL/4 mL) was added. The reaction was allowed to warm up from −78° C. to room temperature over 16 h then slowly quenched with water. The reaction was concentrated and the resulting brown solid was taken up in water and DCM. The organic phase was separated, dried over MgSO$_4$, filtered and concentrated under vacuum to give a brown solid. The solid was dissolved in DMSO and purified by preparatory HPLC to give the title compound (0.1736 g, 9.4%). EI-MS m/z 362(M$^+$) Rt (1.73 min).

Example 33

Preparation of 1-azabicyclo[2.2.2]oct-4-yl(di-3-thienyl)methanol

A solution of t-Butyl lithium (1.7M in pentanes, 5.8 mL, 9.86 mmol) was chilled to −78° C. under Ar. 3-Bromothiophene (0.46 mL, 4.90 mmol) dissolved in THF (4.0 mL) was slowly added to the reaction mixture over 6 min. The reaction was stirred for 30 min and then ethyl 1-azabicyclo[2.2.2]octane-4-carboxylate (0.3132 g, 1.71 mmol) in THF (4 mL) was added. The reaction was allowed to warm up from −78° C. to room temperature over 16 h. After 14 hours, the reaction was slowly quenched with water. EtOAc was added, causing a grey solid to crash out. The solid was filtered off to give the title compound (0.3375 g, 64.6%). EI-MS m/z 306 (M+H)$^+$ Rt (1.27 min).

Example 34

Preparation of 4-[hydroxy(di-3-thienyl)methyl]-1-[2-(phenyloxy)ethyl]-1-azoniabicyclo[2.2.2]octane bromide Following the general procedure outlined in Example 4, 1-azabicyclo[2.2.2]oct-4-yl(di-3-thienyl)methanol (0.0787 g, 0.258 mmol) and 2-bromoethyl phenyl ether (0.0839 g, 0.417 mmol) in 2 MeOH/3 CHCl$_3$/2 CH$_3$CN (5.0 mL) were reacted to give the desired product (0.0709 g, 54.5%). EI-MS m/z 426(M$^+$) Rt (1.85 min).

Example 35

Preparation of 4-[hydroxy(di-3-thienyl)methyl]-1-[3-(phenyloxy)propyl]-1-azoniabicyclo[2.2.2]octane bromide Following the general procedure outlined in Example 4, 1-azabicyclo[2.2.2]oct-4-yl(di-3-thienyl)methanol (0.0808 g, 0.264 mmol) and 3-bromopropyl phenyl ether (0.070 mL, 0.444 mmol) in 2 MeOH/3 CHCl$_3$/2 CH$_3$CN (5.0 mL) were reacted to give the desired product (0.0613 g, 44.7%). EI-MS m/z 440(M$^+$) Rt (2.05 min).

Example 36

Preparation of 1-butyl-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0496 g, 0.169 mmol) and 1-bromobutane (0.030 mL, 0.279 mmol) in 2 CH$_3$CN/3 CHCl$_3$ (4.0 mL) were reacted to give the desired product (0.0509 g, 70.7%). EI-MS m/z 350(M$^+$) Rt (1.83 min).

Example 37

Preparation of 1-hexyl-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0498 g, 0.170 mmol) and 1-bromohexane (0.040 mL, 0.285 mmol) in 2 CH$_3$CN/3 CHCl$_3$ (4.0 mL) were reacted to give the desired product (0.0562 g, 73.0%). EI-MS m/z 378(M$^+$) Rt (2.09 min).

Example 38

Preparation of 4-[hydroxy(diphenyl)methyl]-1-propyl-1-azoniabicyclo[2.2.2]octane bromide Following the general procedure outlined in Example 3, 1-azabicyclo[2.2.2]oct-4-yl(diphenyl)methanol (0.0518 g, 0.176 mmol) and 1-bromopropane (0.030 mL, 0.330 mmol) in 2 CH$_3$CN/3 CHCl$_3$ (4.0 mL) were reacted to give the desired product (0.0548 g, 75.1%). EI-MS m/z 336(M$^+$) Rt (1.97 min).

Example 39

Preparation of 4-[hydroxy(diphenyl)methyl]-1-(3-{[2-(methyloxy)phenyl]oxy}propyl)-1-azoniabicyclo[2.2.2]octane bromide Following the general procedure outlined in Example 3, 1-azabicyclo[2.2.2]oct-4-yl(diphenyl)methanol (0.0467 g, 0.159 mmol) and 1-[(3-bromopropyl)oxy]-2-(methyloxy)benzene (0.0541 g, 0.221 mmol) in 2 CH$_3$CN/3 CHCl$_3$ (4.0 mL) were reacted to give the desired product (0.0625 g, 73.5%). EI-MS m/z 458(M$^+$) Rt (1.96 min).

Example 40

Preparation of 4-[hydroxy(diphenyl)methyl]-1-{3-[(2-hydroxyphenyl)oxy]propyl}-1-azoniabicyclo[2.2.2]octane bromide Following the general procedure outlined in Example 3, 1-azabicyclo[2.2.2]oct-4-yl(diphenyl)methanol (0.0505 g, 0.172 mmol) and 2-[(3-bromopropyl)oxy]phenol (0.0547 g, 0.236 mmol) in 2 $CH_3CN$/3 $CHCl_3$ (4.0 mL) were reacted to give the desired product (0.0675 g, 75.0%). EI-MS m/z 444 ($M^+$) Rt (1.91 min).

Example 41

Preparation of 4-[hydroxy(diphenyl)methyl]-1-[3-(2-naphthalenyloxy)propyl]-1-azoniabicyclo[2.2.2]octane bromide Following the general procedure outlined in Example 3, 1-azabicyclo[2.2.2]oct-4-yl(diphenyl)methanol (0.0472 g, 0.160 mmol) and 3-bromopropyl 2-naphthalenyl ether (0.0618 g, 0.233 mmol) in 2 $CH_3CN$/3 $CHCl_3$ (4.0 mL) were reacted to give the desired product (0.0567 g, 63.7%). EI-MS m/z 478($M^+$) Rt (2.22 min).

Example 42

Preparation of 1-{3-[(3-chlorophenyl)oxy]propyl}-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0479 g, 0.163 mmol) and 3-bromopropyl 3-chlorophenyl ether (0.0552 g, 0.221 mmol) in 2 $CH_3CN$/3 $CHCl_3$ (4.0 mL) were reacted to give the desired product (0.0655 g, 74.4%). EI-MS m/z 462($M^+$) Rt (2.17 min).

Example 43

Preparation of 1-{3-[(4-bromophenyl)oxy]propyl}-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0486 g, 0.165 mmol) and 4-bromophenyl 3-bromopropyl ether (0.0630 g, 0.214 mmol) in 2 $CH_3CN$/3 $CHCl_3$ (4.0 mL) were reacted to give the desired product (0.0731 g, 75.4%). EI-MS m/z 506($M^+$) Rt (2.18 min).

Example 44

Preparation of 4-[hydroxy(diphenyl)methyl]-1-{3-[(4-nitrophenyl)oxy]propyl}-1-azoniabicyclo[2.2.2]octane bromide Following the general procedure outlined in Example 3, 1-azabicyclo[2.2.2]oct-4-yl(diphenyl)methanol (0.0468 g, 0.159 mmol) and 3-bromopropyl 4-nitrophenyl ether (0.0550 g, 0.211 mmol) in 2 $CH_3CN$/3 $CHCl_3$ (4.0 mL) were reacted to give the desired product (0.0590 g, 67.0%). EI-MS m/z 473($M^+$) Rt (2.06 min).

Example 45

Preparation of 4-[hydroxy(diphenyl)methyl]-1-[3-({2-[(phenylmethyl)oxy]phenyl}oxy)propyl]-1-azoniabicyclo[2.2.2]octane bromide Following the general procedure outlined in Example 3, 1-azabicyclo[2.2.2]oct-4-yl(diphenyl)methanol (0.0492 g, 0.168 mmol) and 1-[(3-bromopropyl)oxy]-2-[(phenylmethyl)oxy]benzene (0.0706 g, 0.220 mmol) in 2 $CH_3CN$/3 $CHCl_3$ (4.0 mL) were reacted to give the desired product (0.0735 g, 71.4%). EI-MS m/z 533($M^+$) Rt (2.25 min).

Example 46

Preparation of 1-{3-[(2-bromophenyl)oxy]propyl}-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0472 g, 0.161 mmol) and 2-bromophenyl 3-bromopropyl ether (0.0648 g, 0.220 mmol) in 2 $CH_3CN$/3 $CHCl_3$ (4.0 mL) were reacted to give the desired product (0.0703 g, 74.8%). EI-MS m/z 507($M^+$) Rt (2.18 min).

Example 47

Preparation of 4-[hydroxy(diphenyl)methyl]-1-[3-({4-[(phenylmethyl)oxy]phenyl}oxy)propyl]-1-azoniabicyclo[2.2.2]octane bromide Following the general procedure outlined in Example 3, 1-azabicyclo[2.2.2]oct-4-yl(diphenyl)methanol (0.0479 g, 0.163 mmol) and 1-[(3-bromopropyl)oxy]-4-[(phenylmethyl)oxy]benzene (0.0730 g, 0.227 mmol) in 2 $CH_3CN$/3 $CHCl_3$ (4.0 mL) were reacted to give the desired product (0.0833 g, 83.3%). EI-MS m/z 534($M^+$) Rt (2.31 min).

Example 48

Preparation of 4-[hydroxy(diphenyl)methyl]-1-[3-(methyloxy)propyl]-1-azoniabicyclo[2.2.2]octane bromide Following the general procedure outlined in Example 3, 1-azabicyclo[2.2.2]oct-4-yl(diphenyl)methanol (0.0632 g, 0.215 mmol) and 3-bromopropyl methyl ether (0.0461 g, 0.301 mmol) in 2 $CH_3CN$/3 $CHCl_3$ (4.0 mL) were reacted to give the desired product (0.0826 g, 86.0%). EI-MS m/z 366 ($M^+$) Rt (1.55 min).

Example 49

Preparation of 4-[hydroxy(diphenyl)methyl]-1-(2-propen-1-yl)-1-azoniabicyclo[2.2.2]octane bromide Following the general procedure outlined in Example 3, 1-azabicyclo[2.2.2]oct-4-yl(diphenyl)methanol (0.0577 g, 0.197 mmol) and 3-bromo-1-propene (0.025 mL, 0.289 mmol) in 2 $CH_3CN$/3 $CHCl_3$ (4.0 mL) were reacted to give the desired product (0.0646 g, 79.8%). EI-MS m/z 334($M^+$) Rt (1.54 min).

Example 50

Preparation of 4-[hydroxy(diphenyl)methyl]-1-(3-{[4-(methyloxy)phenyl]oxy}propyl)-1-azoniabicyclo[2.2.2]octane bromide Following the general procedure outlined in Example 3, 1-azabicyclo[2.2.2]oct-4-yl(diphenyl)methanol (0.0483 g, 0.164 mmol) and 1-[(3-bromopropyl)oxy]-4-(methyloxy)benzene (0.052 g, 0.21 mmol) in 2 $CH_3CN$/3 $CHCl_3$ (4.0 mL) were reacted to give the desired product (0.0687 g, 77.5%). EI-MS m/z 458($M^+$) Rt (2.03 min).

Example 51

Preparation of [1-(2-aminoethyl)-1-azoniabicyclo[2.2.2]oct-4-yl](diphenyl)methanolate trifluoroacetate To a solution of 1-[2-(1,3-dioxo-1,3-dihydro-2H-isoindol-2-yl)ethyl]-4-[hydroxy(diphenyl)methyl]-1-azoniabicyclo[2.2.2]octane bromide (0.078g, 0.142 mmol) in EtOH (4.0 mL) was added hydrazine (0.25 mL, 7.96 mmol). The solution was stirred at room temperature for 16 h and then filtered. The filtrate was concentrated and taken up in 2.5 mL of DMSO and purified by preparatory HPLC (with TFA) to give the title compound (0.0200 g, 31.2%). EI-MS m/z 338($M^+$) Rt (1.28 min).

Example 52

Preparation of 4-[bis(4-fluorophenyl)(hydroxy)methyl]-1-[3-(phenyloxy)propyl]-1-azoniabicyclo[2.2.2]octane bromide

1-azabicyclo[2.2.2]oct-4-yl[bis(4-fluorophenyl)]methanol

A solution of 4-fluorophenylmagnesiumbromide (1.0 M in THF, 4.4 mL, 4.4 mmol) was chilled down to 0° C. under Ar. Ethyl 1-azabicyclo[2.2.2]octane-4-carboxylate (0.1973 g, 1.08 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated $NH_4Cl$, and concentrated under vacuum. The resulting residue was treated with $H_2O$ and extracted with EtOAc. The combined organic layers were dried with $MgSO_4$, filtered, and concentrated under vacuum to yield the desired product (0.3152 g, 88.9%). EI-MS m/z 330($M+H^+$) Rt (1.65 min).

4-[bis(4-fluorophenyl)(hydroxy)methyl]-1-[3-(phenyloxy)propyl]-1-azoniabicyclo[2.2.2]octane bromide Following the general procedure outlined in Example 3, 1-azabicyclo[2.2.2]oct-4-yl[bis(4-fluorophenyl)]methanol (0.0538 g, 0.163 mmol) and 3-bromopropyl phenyl ether (0.0386 mL, 0.245 mmol) in 2 $CH_3CN$/3 $CHCl_3$ (4.0 mL) were reacted to give the desired product (0.058 g, 65.2%). EI-MS m/z 464($M^+$) Rt (2.16 min).

Example 53

Preparation of 4-[bis(4-fluorophenyl)(hydroxy)methyl]-1-{2-[(phenylmethyl)oxy]ethyl}-1-azoniabicyclo[2.2.2]octane bromide Following the general procedure outlined in Example 3, 1-azabicyclo[2.2.2]oct-4-yl[bis(4-fluorophenyl)]methanol (0.0489 g, 0.148 mmol) and 2-bromoethyl phenylmethyl ether (0.0352 mL, 0.222 mmol) in 2 $CH_3CN$/3 $CHCl_3$ (4.0 mL) were reacted to give the desired product (0.0534 g, 66.1%). EI-MS m/z 464($M^+$) Rt (1.99 min).

Example 54

Preparation of 4-(hydroxy{bis[3-(methyloxy)phenyl]}methyl)-1-[3-(phenyloxy)propyl]-1-azoniabicyclo[2.2.2]octane bromide

1-azabicyclo[2.2.2]oct-4-yl{bis[3-(methyloxy)phenyl]}methanol

A solution of 3-(methyloxy)phenylmagnesiumbromide (1.0 M in THF, 3.3 mL, 3.3 mmol) was chilled down to 0° C. under Ar. Ethyl 1-azabicyclo[2.2.2]octane-4-carboxylate (0.1608 g, 0.877 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated $NH_4Cl$, and concentrated under vacuum. The resulting residue was treated with $H_2O$ and extracted with EtOAc. The combined organic layers were dried with $MgSO_4$, filtered, and concentrated under vacuum to yield the desired product (0.2881 g, 92.9%). EI-MS m/z 354($M+H^+$) Rt (1.46 min).

4-(hydroxy{bis[3-(methyloxy)phenyl]}methyl)-1-[3-(phenyloxy)propyl]-1-azoniabicyclo[2.2.2]octane bromide Following the general procedure outlined in Example 3, 1-azabicyclo[2.2.2]oct-4-yl{bis[3-(methyloxy)phenyl]}methanol (0.0506 g, 0.143 mmol) and 3-bromopropyl phenyl ether (0.0338 mL, 0.214 mmol) in 2 $CH_3CN$/3 $CHCl_3$ (4.0 mL) were reacted to give the desired product (0.027 g, 33.2%). EI-MS m/z 488($M^+$) Rt (2.02 min).

Example 55

Preparation of 4-(hydroxy{bis[3-(methyloxy)phenyl]}methyl)-1-{2-[(phenylmethyl)oxy]ethyl}-1-azoniabicyclo[2.2.2]octane bromide Following the general procedure outlined in Example 3, 1-azabicyclo[2.2.2]oct-4-yl {bis[3-(methyloxy)phenyl]}methanol (0.0538 g, 0.152 mmol) and 2-bromoethyl phenylmethyl ether (0.0361 mL, 0.228 mmol) in 2 $CH_3CN$/3 $CHCl_3$ (4.0 mL) were reacted to give the desired product (0.0292 g, 33.8%). EI-MS m/z 488($M^+$) Rt (2.03 min).

Example 56

Preparation of 4-(hydroxy{bis[4-(methyloxy)phenyl]}methyl)-1-[3-(phenyloxy)propyl]-1-azoniabicyclo[2.2.2]octane bromide 1-azabicyclo[2.2.2]oct-4-yl{bis[4-(methyloxy)phenyl]}methanol A solution of 4-(methyloxy)phenylmagnesiumbromide (0.5 M in THF, 6.5 mL, 3.25 mmol) was chilled down to 0° C. under Ar. Ethyl 1-azabicyclo[2.2.2]octane-4-carboxylate (0.1587 g, 0.866 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated NH$_4$Cl, and concentrated under vacuum. The resulting residue was treated with H$_2$O and extracted with EtOAc. The combined organic layers were dried with MgSO$_4$, filtered, and concentrated under vacuum to yield the desired product (0.273 g, 89.0%). EI-MS m/z 354(M+H$^+$) Rt (1.74 min).

4-(hydroxy{bis[3-(methyloxy)phenyl]}methyl)-1-[3-(phenyloxy)propyl]-1-azoniabicyclo[2.2.2]octane bromide Following the general procedure outlined in Example 3, 1-azabicyclo[2.2.2]oct-4-yl{bis[4-(methyloxy)phenyl]}methanol (0.0525 g, 0.148 mmol) and 3-bromopropyl phenyl ether (0.0351 mL, 0.222 mmol) in 2 CH$_3$CN/3 CHCl$_3$ (4.0 mL) were reacted to give the desired product (0.0515 g, 61.0%). EI-MS m/z 488(M$^+$) Rt (2.04 min).

Example 57

Preparation of 4-(hydroxy{bis[4-(methyloxy)phenyl]}methyl)-1-{2-[(phenylmethyl)oxy]ethyl}-1-azoniabicyclo[2.2.2]octane bromide Following the general procedure outlined in Example 3, 1-azabicyclo[2.2.2]oct-4-yl{bis[4-(methyloxy)phenyl]}methanol (0.0498 g, 0.141 mmol) and 2-bromoethyl phenylmethyl ether (0.0334 mL, 0.211 mmol) in 2 CH$_3$CN/3 CHCl$_3$ (4.0 mL) were reacted to give the desired product (0.0374 g, 46.7%). EI-MS m/z 488(M$^+$) Rt (1.94 min).

Example 58

Preparation of 4-[bis(3-fluorophenyl)(hydroxy)methyl]-1-[3-(phenyloxy)propyl]-1-azoniabicyclo[2.2.2]octane bromide 1-azabicyclo[2.2.2]oct-4-yl[bis(3-fluorophenyl)]methanol A solution of 3-fluorophenylmagnesiumbromide (1.0 M in THF, 3.3 mL, 3.3 mmol) was chilled down to 0° C. under Ar. Ethyl 1-azabicyclo[2.2.2]octane-4-carboxylate (0.1756 g, 0.958 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated NH$_4$Cl, and concentrated under vacuum. The resulting residue was treated with H$_2$O and extracted with EtOAc. The combined organic layers were dried with MgSO$_4$, filtered, and concentrated under vacuum to yield the desired product (0.242 g, 76.7%). EI-MS m/z 330(M+H$^+$) Rt (1.45 min).

4-hydroxy{bis[3-(methyloxy)phenyl]}methyl)-1-[3-(phenyloxy)propyl]-1-azoniabicyclo[2.2.2]octane bromide Following the general procedure outlined in Example 3, 1-azabicyclo[2.2.2]oct-4-yl[bis(3-fluorophenyl)]methanol (0.0515 g, 0.156 mmol) and 3-bromopropyl phenyl ether (0.0370 mL, 0.234 mmol) in 2 CH$_3$CN/3 CHCl$_3$ (4.0 mL) were reacted to give the desired product (0.0381 g, 44.8%). EI-MS m/z 464(M$^+$) Rt (2.01 min).

Example 59

Preparation of 4-[bis(3-fluorophenyl)(hydroxy)methyl]-1-{2-[(phenylmethyl)oxy]ethyl}-1-azoniabicyclo[2.2.2]octane bromide Following the general procedure outlined in Example 3, 1-azabicyclo[2.2.2]oct-4-yl[bis(3-fluorophenyl)]methanol (0.0507 g, 0.154 mmol) and 2-bromoethyl phenylmethyl ether (0.0365 mL, 0.230 mmol) in 2 CH$_3$CN/3 CHCl$_3$ (4.0 mL) were reacted to give the desired product (0.0362 g, 43.2%). EI-MS m/z 464(M+) Rt (2.02 min).

Example 60

Preparation of 4-{hydroxy[bis(3-methylphenyl)]methyl}-1-[3-(phenyloxy)propyl]-1-azoniabicyclo[2.2.2]octane bromide 1-azabicyclo[2.2.2]oct-4-yl[bis(3-methylphenyl)]methanol A solution of 3-methylphenylmagnesiumbromide (1.0 M in THF, 3.3 mL, 3.3 mmol) was chilled down to 0° C. under Ar. Ethyl 1-azabicyclo[2.2.2]octane-4-carboxylate (0.1484 g, 0.810 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated NH$_4$Cl, and concentrated under vacuum. The resulting residue was treated with H$_2$O and extracted with EtOAc. The combined organic layers were dried with MgSO$_4$, filtered, and concentrated under vacuum to yield the desired product (0.1806 g, 69.4%). EI-MS m/z 322(M+H$^+$) Rt (1.54 min).

4-(hydroxy{bis[3-(methyloxy)phenyl]}methyl)-1-[3-(phenyloxy)propyl]-1-azoniabicyclo[2.2.2] octane bromide Following the general procedure outlined in Example 3, 1-azabicyclo[2.2.2]oct-4-yl[bis(3-methylphenyl)]methanol (0.0487 g, 0.151 mmol) and 3-bromopropyl phenyl ether (0.0358 mL, 0.227 mmol) in 2 CH$_3$CN/3 CHCl$_3$ (4.0 mL) were reacted to give the desired product (0.0284 g, 34.9%). EI-MS m/z 456(M$^+$) Rt (2.14 min).

Example 61

Preparation of 4-{hydroxy[bis(3-methylphenyl)]methyl}-1-{2-[(phenylmethyl)oxy]ethyl}-1-azoniabicyclo[2.2.2]octane bromide Following the general procedure outlined in Example 4, 1-azabicyclo[2.2.2]oct-4yl[bis(3-methylphenyl)]methanol (0.0496 g, 0.154 mmol) and 2-bromoethyl phenylmethyl ether (0.0364 mL, 0.230 mmol) in 2 CH$_3$CN/3 CHCl$_3$ (4.0 mL) were reacted to give the desired product (0.0091 g, 11.0%). EI-MS m/z 456(M$^+$) Rt (2.20 min).

Example 62

Preparation of 4-{hydroxy[bis(4-methylphenyl)] methyl}-1-[3-(phenyloxy)propyl]-1-azoniabicyclo [2.2.2]octane bromide 1-azabicyclo[2.2.2]oct-4-yl[bis(4-methylphenyl)] methanol A solution of 4-methylphenylmagnesiumbromide (1.0 M in THF, 3.3 mL, 3.3 mmol) was chilled down to 0° C. under Ar. Ethyl 1-azabicyclo[2.2.2]octane-4-carboxylate (0.1509 g, 0.823 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated NH$_4$Cl, and concentrated under vacuum. The resulting residue was treated with H$_2$O and extracted with EtOAc. The combined organic layers were dried with MgSO$_4$, filtered, and concentrated under vacuum to yield the desired product (0.2291 g, 86.6%). EI-MS m/z 322(M+H$^+$) Rt (1.57 min).

4-(hydroxy{bis[3-(methyloxy)phenyl]}methyl)-1-[3-(phenyloxy)propyl]-1-azoniabicyclo[2.2.2]octane bromide Following the general procedure outlined in Example 3, 1-azabicyclo[2.2.2]oct-4-yl[bis(4-methylphenyl)]methanol (0.0618 g, 0.192 mmol) and 3-bromopropyl phenyl ether (0.0454 mL, 0.288 mmol) in 2 CH$_3$CN/3 CHCl$_3$ (4.0 mL) were reacted to give the desired product (0.0427 g, 41.5%). EI-MS m/z 456(M$^+$) Rt (1.99 min).

Example 63

Preparation of 4-{hydroxy[bis(4-methylphenyl)] methyl}-1-{2-[(phenylmethyl)oxy]ethyl}-1-azoniabicyclo[2.2.2]octane bromide Following the general procedure outlined in Example 3, 1-azabicyclo[2.2.2]oct-4-yl[bis(4-methylphenyl)]methanol (0.0525 g, 0.163 mmol) and 2-bromoethyl phenylmethyl ether (0.0387 mL, 0.245 mmol) in 2 CH$_3$CN/3 CHCl$_3$ (4.0 mL) were reacted to give the desired product (0.0465 g, 53.1%). EI-MS m/z 456(M$^+$) Rt (2.09 min).

Example 64

Preparation of 4-[hydroxy(di-2-naphthalenyl)methyl]-1-[3-(phenyloxy)propyl]-1-azoniabicyclo [2.2.2]octane bromide 1-azabicyclo[2.2.2]oct-4-yl(di-2-naphthalenyl) methanol A solution of (2-naphthalenyl)magnesiumbromide (0.5 M in THF, 6.5 mL, 3.25 mmol) was chilled down to 0° C. under Ar. Ethyl 1-azabicyclo[2.2.2]octane-4-carboxylate (0.1597 g, 0.871 mmol) in THF (4 mL) was slowly added to the reaction mixture at 0° C. over 20 min. The reaction was allowed to warm up to room temperature and then heated at 60° C. for 16 h. The reaction was chilled in an ice bath, quenched with saturated NH$_4$Cl, and concentrated under vacuum. The resulting residue was treated with H$_2$O and extracted with EtOAc. The combined organic layers were dried with MgSO$_4$, filtered, and concentrated under vacuum to yield the desired product (0.265 g, 77.3%). EI-MS m/z 394(M+H$^+$) Rt (1.90 min).

4-(hydroxy{bis[3-(methyloxy)phenyl]}methyl)-1-[3-(phenyloxy)propyl]-1-azoniabicyclo[2.2.2]octane bromide Following the general procedure outlined in Example 3, 1-azabicyclo[2.2.2]oct-4-yl(di-2-naphthalenyl)methanol (0.0547 g, 0.139 mmol) and 3-bromopropyl phenyl ether (0.0329 mL, 0.209 mmol) in 2 CH$_3$CN/3 CHCl$_3$ (4.0 mL) were reacted to give the desired product (0.0268 g, 31.7%). EI-MS m/z 528(M$^+$) Rt (2.88 min).

Example 65

Preparation of 4-[hydroxy(di-2-naphthalenyl)methyl]-1-{2-[(phenylmethyl)oxy]ethyl}-1-azoniabicyclo[2.2.2]octane bromide Following the general procedure outlined in Example 3, 1-azabicyclo[2.2.2]oct-4-yl(di-2-naphthalenyl)methanol (0.063.7 g, 0.162 mmol) and 2-bromoethyl phenylmethyl ether (0.0384 mL, 0.243 mmol) in 2 CH$_3$CN/3 CHCl$_3$ (4.0 mL) were reacted to give the desired product (0.0246 g, 25.0%). EI-MS m/z 528(M$^+$) Rt (2.36 min).

Example 66

Preparation of 1-{3-[(2-fluorophenyl)oxy]propyl}-4-[hydroxy(diphenyl)methyl]-1-azoniabicyclo[2.2.2] octane bromide 3-bromopropyl 2-fluorophenyl ether To a solution of 2-fluorophenol (0.040 mL, 0.448 mmol) in acetonitrile (4 mL) was added 1,3-dibromopropane (0.450 mL, 4.43 mmol) followed by Cs$_2$CO$_3$ (0.232 g, 0.713 mmol). The reaction mixture was stirred for 24 h and then concentrated under vacuum. The resulting residue was treated with H$_2$O (4 mL) and extracted with DCM (8 mL). The organic layer was dried through a phase separator and concentrated under vacuum. The residue was taken up in DMSO and purified by preparatory HPLC (without TFA) to give the title compound (0.0274 g, 26.2%). EI-MS Rt (2.24 min).

1-{3-[(2-fluorophenyl)oxy]propyl}-4-[hydroxy (diphenyl)methyl]-1-azoniabicyclo[2.2.2]octane bromide Following the general procedure outlined in Example 3, 1-azabicyclo[2.2.2]oct-4-yl(diphenyl)methanol (0.0282 g, 0.0960 mmol) and 3-bromopropyl 2-fluorophenyl ether (0.0274 g, 0.118 mmol) in 2 CH$_3$CN/3 CHCl$_3$ (4.0 mL) were reacted to give the desired product (0.0345 g, 68.3%). EI-MS m/z 446(M$^+$) Rt (1.96 min).

Example 67

Preparation of 1-{3-[(3-fluorophenyl)oxy]propyl}-4-[hydroxy(diphenyl)methyl]-1-azoniabicyclo[2.2.2]octane bromide 3-bromopropyl 3-fluorophenyl ether To a solution of 3-fluorophenol (0.040 mL, 0.448 mmol) in acetonitrile (4 mL) was added 1,3-dibromopropane (0.450 mL, 4.43 mmol) followed by $Cs_2CO_3$ (0.246 g, 0.756 mmol). The reaction mixture was stirred for 24 h and then concentrated under vacuum. The resulting residue was treated with $H_2O$ (4 mL) and extracted with DCM (8 mL). The organic layer was dried through a phase separator and concentrated under vacuum. The residue was taken up in DMSO and purified by preparatory HPLC (without TFA) to give the title compound (0.0137 g, 13.2%). EI-MS Rt (2.28 min).

1-{3-[(3-fluorophenyl)oxy]propyl}-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0137 g, 0.0467 mmol) and 3-bromopropyl 3-fluorophenyl ether (0.0137 g, 0.0588 mmol) in 2 $CH_3CN$/3 $CHCl_3$ (4.0 mL) were reacted to give the desired product (0.0130 g, 53.1%). EI-MS m/z 446($M^+$) Rt (2.03 min).

Example 68

Preparation of 1-{3-[(4-fluorophenyl)oxy]propyl}-4-[hydroxy(diphenyl)methyl]-1-azoniabicyclo[2.2.2]octane bromide 3-bromopropyl 4-fluorophenyl ether To a solution of 4-fluorophenol (0.0567 g, 0.506 mmol) in acetonitrile (4 mL) was added 1,3-dibromopropane (0.520 mL, 5.12 mmol) followed by $Cs_2CO_3$ (0.252 g, 0.774 mmol). The reaction mixture was stirred for 24 h and then concentrated under vacuum. The resulting residue was treated with $H_2O$ (4 mL) and extracted with DCM (8 mL). The organic layer was dried through a phase separator and concentrated under vacuum. The residue was taken up in DMSO and purified by preparatory HPLC (without TFA) to give the title compound (0.0173 g, 14.7%). EI-MS Rt (2.25 min).

1-{3-[(4-fluorophenyl)oxy]propyl}-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0182 g, 0.0621 mmol) and 3-bromopropyl 4-fluorophenyl ether (0.0173 g, 0.0742 mmol) in 2 $CH_3CN$/3 $CHCl_3$ (4.0 mL) were reacted to give the desired product (0.0143 g, 43.7%). EI-MS m/z 446($M^+$) Rt (1.96 min).

Example 69

Preparation of 1-[3-(3-biphenylyloxy)propyl]-4-[hydroxy(diphenyl)methyl]-1-azoniabicyclo[2.2.2]octane bromide 3-biphenylyl 3-bromopropyl ether To a solution of 3-biphenylol (0.0574 g, 0.337 mmol) in acetonitrile (4 mL) was added 1,3-dibromopropane (0.340 mL, 3.35 mmol) followed by $Cs_2CO_3$ (0.172 g, 0.529 mmol). The reaction mixture was stirred for 24 h and then concentrated under vacuum. The resulting residue was treated with $H_2O$ (4 mL) and extracted with DCM (8 mL). The organic layer was dried through a phase separator and concentrated under vacuum. The residue was taken up in DMSO and purified by preparatory HPLC (without TFA) to give the title compound (0.0568 g, 57.8%). EI-MS Rt (2.59 min).

1-[3-(3-biphenylyloxy)propyl]-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0433 g, 0.148 mmol) and 3-biphenylyl 3-bromopropyl ether (0.0568 g, 0.196 mmol) in 2 $CH_3CN$/3 $CHCl_3$ (4.0 mL) were reacted to give the desired product (0.0610 g, 70.6%). EI-MS m/z 504($M^+$) Rt (2.37 min).

Example 70

Preparation of 1-[3-(4-biphenylyloxy)propyl]-4-[hydroxy(diphenyl)methyl]-1-azoniabicyclo[2.2.2]octane bromide 4-biphenylyl 3-bromopropyl ether To a solution of 4-biphenylol (0.0514 g, 0.302 mmol) in acetonitrile (4 mL) was added 1,3-dibromopropane (0.310 mL, 3.05 mmol) followed by $Cs_2CO_3$ (0.154 g, 0.472 mmol). The reaction mixture was stirred for 24h and then concentrated under vacuum. The resulting residue was treated with $H_2O$ (4 mL) and extracted with DCM (8 mL). The organic layer was dried through a phase separator and concentrated under vacuum. The residue was taken up in DMSO and purified by preparatory HPLC (without TFA) to give the title compound (0.0562 g, 64.0%). EI-MS Rt (2.62 min).

1-[3-(4-biphenylyloxy)propyl]-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0437 g, 0.144 mmol) and 4-biphenylyl 3-bromopropyl ether (0.0562 g, 0.194 mmol) in 2 $CH_3CN$/3 $CHCl_3$ (4.0 mL) were reacted to give the desired product (0.0655 g, 75.2%). EI-MS m/z 504($M^+$) Rt (2.24 min).

Example 71

Preparation of 4-[hydroxy(diphenyl)methyl]-1-{3-[(3-nitrophenyl)oxy]propyl}-1-azoniabicyclo[2.2.2]octane bromide 3-bromopropyl 3-nitrophenyl ether To a solution of 3-nitrophenol (0.0689 g, 0.495 mmol) in acetonitrile (4 mL) was added 1,3-dibromopropane (0.500 mL, 3.05 mmol) followed by $Cs_2CO_3$ (0.244 g, 0.748 mmol).

The reaction mixture was stirred for 24 h and then concentrated under vacuum. The resulting residue was treated with H$_2$O (4 mL) and extracted with DCM (8 mL). The organic layer was dried through a phase separator and concentrated under vacuum. The residue was taken up in DMSO and purified by preparatory HPLC (without TFA) to give the title compound (0.0730 g, 56.6%). EI-MS Rt (2.20 min).

4-[hydroxy(diphenyl)methyl]-1-{3-[(3-nitrophenyl)oxy]propyl}-1-azoniabicyclo[2.2.2]octane bromide Following the general procedure outlined in Example 3, 1-azabicyclo[2.2.2]oct-4-yl(diphenyl)methanol (0.0608 g, 0.207 mmol) and 3-bromopropyl 3-nitrophenyl ether (0.0730 g, 0.281 mmol) in 2 CH$_3$CN/3 CHCl$_3$ (4.0 mL) were reacted to give the desired product (0.0942 g, 82.2%). EI-MS m/z 474(M$^+$) Rt (2.04 min).

Example 72

Preparation of 4-[hydroxy(diphenyl)methyl]-1-{3-[(2-methylphenyl)oxy]propyl}-1-azoniabicyclo[2.2.2]octane bromide 3-bromopropyl 2-methylphenyl ether To a solution of 2-methylphenol (0.0954 g, 0.924 mmol) in acetonitrile (4 mL) was added 1,3-dibromopropane (1.00 mL, 9.85 mmol) followed by Cs$_2$CO$_3$ (0.469 g, 1.44 mmol). The reaction mixture was stirred for 24 h and then concentrated under vacuum. The resulting residue was treated with H$_2$O (4 mL) and extracted with DCM (8 mL). The organic layer was dried through a phase separator and concentrated under vacuum. The residue was taken up in DMSO and purified by preparatory HPLC (without TFA) to give the title compound (0.0934 g, 44.1%). EI-MS Rt (2.45 min).

4-[hydroxy(diphenyl)methyl]-1-{3-[(2-methylphenyl)oxy]propyl}-1-azoniabicyclo[2.2.2]octane bromide Following the general procedure outlined in Example 3, 1-azabicyclo[2.2.2]oct-4-yl(diphenyl)methanol (0.0447 g, 0.152 mmol) and 3-bromopropyl 2-methylphenyl ether (0.0934 g, 0.407 mmol) in 2 CH$_3$CN/3 CHCl$_3$ (4.0 mL) were reacted to give the desired product (0.0586 g, 76.5%). EI-MS m/z 442(M$^+$) Rt (2.17 min).

Example 73

Preparation of 1-(3-{[3-(diethylamino)phenyl]oxy}propyl)-4-[hydroxy(diphenyl)methyl]-1-azoniabicyclo[2.2.2]octane bromide 3-[3-bromopropyl)oxy]-N,N-diethylaniline To a solution of 3-(diethylamino)phenol (0.0104 g, 0.631 mmol) in acetonitrile (4 mL) was added 1,3-dibromopropane (0.640 mL, 6.30 mmol) followed by Cs$_2$CO$_3$ (0.313 g, 0.961 mmol). The reaction mixture was stirred for 24 h and then concentrated under vacuum. The resulting residue was treated with H$_2$O (4 mL) and extracted with DCM (8 mL). The organic layer was dried through a phase separator and concentrated under vacuum. The residue was taken up in DMSO and purified by preparatory HPLC (without TFA) to give the title compound (0.0314 g, 17.4%). EI-MS m/z 286 (M+H$^+$) Rt (1.59 min).

1-(3-{[3-(diethylamino)phenyl]oxy}propyl-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0257 g, 0.0876 mmol) and 3-[(3-bromopropyl)oxy]-N,N-diethylaniline (0.0314 g, 0.110 mmol) in 2 CH$_3$CN/3 CHCl$_3$ (4.0 mL) were reacted to give the desired product (0.032.0 g, 63.0%). EI-MS m/z 500(M$^+$) Rt (1.58 min).

Example 74

Preparation of 1-{3-[(4-cyanophenyl)oxy]propyl}-4-[hydroxy(diphenyl)methyl]-1-azoniabicyclo[2.2.2]octane bromide 4-[(3-bromopropyl)oxy]benzonitrile To a solution of 4-hydroxybenzonitrile (0.109 g, 0.913 mmol) in acetonitrile (4 mL) was added 1,3-dibromopropane (0.930 mL, 9.16 mmol) followed by Cs$_2$CO$_3$ (0.439 g, 1.35 mmol). The reaction mixture was stirred for 24 h and then concentrated under vacuum. The resulting residue was treated with H$_2$O (4 mL) and extracted with DCM (8 mL). The organic layer was dried through a phase separator and concentrated under vacuum. The residue was taken up in DMSO and purified by preparatory HPLC (without TFA) to give the title compound (0.156 g, 71.4%). EI-MS Rt (2.10 min).

1-{3-[(4-cyanophenyl)oxy]propyl}-4-[hydroxy(diphenyl)methyl]-1-azoniabicyclo[2.2.2]octane bromide Following the general procedure outlined in Example 3, 1-azabicyclo[2.2.2]oct-4-yl(diphenyl)methanol (0.0520 g, 0.177 mmol) and 4-[(3-bromopropyl)oxy]benzonitrile (0.156 g, 0.652 mmol) in 2 CH$_3$CN/3 CHCl$_3$ (4.0 mL) were reacted to give the desired product (0.0726 g, 76.8%). EI-MS m/z 453(M$^+$) Rt (1.86 min).

Example 75

Preparation of 4-[hydroxy(diphenyl)methyl]-1-[2-({[3-(methyloxy)phenyl]methyl}oxy)ethyl]-1-azoniabicyclo[2.2.2]octane bromide 2-({[3-(methyloxy)phenyl]methyl}oxy)ethanol Ethylene glycol (0.084 mL, 1.5 mmol) was added to NaH (38 mg, 1.52 mmol, 95% in oil) in THF (3 mL) (caution: exotherm). m-Methoxybenzyl chloride (0.21 mL, 1.5 mmol) was added to the reaction, and the residual m-methoxybenzyl chloride was transferred to the reaction tube with additional THF (1 mL). (Bu)$_4$NI (55 mg, 0.15 mmol) was then added, and the reaction was heated at 60° C. for 18 h and then cooled to room temperature for 4 h. H$_2$O (2 mL) and EtOAc (2 mL) were added, and the layers were separated via pipette. The aqueous layer was extracted with EtOAc (1×1 mL), and the combined organic layers were concentrated. The crude product was purified on a Biotage 12+M cartridge (8 g silica) eluting with 30% EtOAc/hexanes at 5 mL/min to give the title compound (114 mg, 42%). The product was characterized by $^1$H NMR (400 MHz) in CDCl$_3$.

1-{[(2-bromoethyl)oxy]methyl}-3-(methyloxy)benzene

A solution of N-bromosuccinimide (272 mg, 1.53 mmol) in DCM (2.5 mL) was added resin-bound triphenylphosphine (510 mg, 1.53 mEquiv, Fluka) in DCM (2.5 mL). The reaction was stirred at room temperature for 10 min. A solution of 2-({[3-(methyloxy)phenyl]methyl}oxy)ethanol (114 mg, 0.626 mmol) in DCM (1.5 mL) was added to the reaction, and the residual alcohol was transferred with additional DCM (1.5 mL). The reaction vessel was wrapped in aluminum foil and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (160 mg). The product was characterized by $^1$H NMR (400 MHz) in $CDCl_3$.

4-[hydroxy(diphenyl)methyl]-1-[2-({[3-(methyloxy)phenyl]methyl}oxy)ethyl]-1-azoniabicyclo[2.2.2]octane bromide 1-Azabicyclo[2.2.2]oct-4-yl(diphenyl)methanol (30 mg, 0.102 mmol) was added to a solution of 1-{[(2-bromoethyl)oxy]methyl}-3-(methyloxy)benzene (35 mg, 0.143 mmol) in 2 $CH_3CN$/3 $CHCl_3$ (3 mL). The reaction was heated at 60° C. for 96 h. The reaction was concentrated, and the crude product was washed with EtOAc (3×1 mL) and then MeOH (1×1 mL). The product was dried under high vacuum to give the title compound (7.7 mg, 14%). LC/MS ESI $R_T$ 1.97 min M$^+$ 458

Example 76

Preparation of 1-[2-({[4-(1,1-dimethylethyl)phenyl]methyl}oxy)ethyl]-4-[hydroxy(diphenyl)methyl]-1-azoniabicyclo[2.2.2]octane bromide

2-({[4-(1-dimethylethyl)phenyl]methyl}oxy)ethanol

Ethylene glycol (0.084 mL, 1.5 mmol) was added to NaH (38 mg, 1.52 mmol, 95% in oil) in THF (3 mL). 1-(Bromomethyl)-4-(1,1-dimethylethyl)benzene (0.28 mL, 1.5 mmol) was added to the reaction, and the residual 1-(bromomethyl)-4-(1,1-dimethylethyl)benzene was transferred to the reaction tube with additional THF (1 mL). $(Bu)_4NI$ (55 mg, 0.15 mmol) was then added, and the reaction heated at 60° C. for 18 h and then rt for 4 h. $H_2O$ (2 mL) and EtOAc (2 mL) were added, and the layers were separated via pipette. The aqueous layer was extracted with EtOAc (1×1 mL), and the combined organic layers were concentrated. The crude product was purified on a SPE cartridge (5 g silica) eluting with the following 10 mL fractions: 10% EtOAc/hexanes (fractions 1,2), 30% EtOAc/hexanes (fractions 3,4), and 50% EtOAc/hexanes (fractions 5,6) to give the title compound (312 mg, 51%). The product was characterized by $^1$H NMR (400 MHz) in $CDCl_3$.

1-{[(2-bromoethyl)oxy]methyl}-4-(1,1-dimethylethyl)benzene

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution of 2-({[4-(1,1-dimethylethyl)phenyl]methyl}oxy)ethanol (160 mg, 0.768 mmol) in DCM (1.5 mL) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (25 mg, 12%). The product was characterized by $^1$H NMR (400 MHz) in $CDCl_3$.

1-[2-({[4-(1,1-dimethylethyl)phenyl]methyl}oxy)ethyl]-4-[hydroxy(diphenyl)methyl]-1-azoniabicyclo[2.2.2]octane bromide 1-Azabicyclo[2.2.2]oct-4-yl(diphenyl)methanol (30 mg, 0.102 mmol) was added to a solution of 1-{[(2-bromoethyl)oxy]methyl}-4-(1,1-dimethylethyl)benzene (25 mg, 0.143 mmol) in 2:3 $CH_3CN$/$CHCl_3$ (3 mL), and the reaction was heated at 60° C. for 96 h. The reaction was concentrated, and the crude product was washed with EtOAc (3×1 mL). The product was dried under high vacuum to give the title compound (9 mg, 16%). LC/MS ESI $R_T$ 2.28 min M$^+$ 484

Example 77

Preparation of 1-(2-{[(4-fluorophenyl)methyl]oxy}ethyl)-4-[hydroxy(diphenyl)methyl]-1-azoniabicyclo[2.2.2]octane bromide

2-{[(4-fluorophenyl)methyl]oxy}ethanol

Ethylene glycol (0.084 mL, 1.5 mmol) was added to NaH (38 mg, 1.52 mmol, 95% in oil) in THF (3 mL). 1-(Bromomethyl)-4-fluorobenzene (0.19 mL, 1.5 mmol) was added to the reaction, and the residual 1-(bromomethyl)-4-fluorobenzene was transferred to the reaction tube with additional THF (1 mL). $(Bu)_4NI$ (55 mg, 0.15 mmol) was added, and the reaction was heated at 60° C. for 18 h and then rt for 4 h. $H_2O$ (2 mL) and EtOAc (2 mL) were added, and the layers were separated via pipette. The aqueous layer was extracted with EtOAc (1×1 mL), and the combined organic layers were concentrated. The crude product was purified on a SPE cartridge (5 g silica) eluting with the following 10 mL fractions: 30% EtOAc/hexanes (fractions 1,2), 50% EtOAc/hexanes (fraction 3), and 75% EtOAc/hexanes (fraction 4) to give the title compound (122 mg, 48%). The product was characterized by 1H NMR (400 MHz) in $CDCl_3$.

1-{[(2-bromoethyl)oxy]methyl}-4-fluorobenzene

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution of 2-{[(4-fluorophenyl)methyl]oxy}ethanol (122 mg, 0.717 mmol) in DCM (1.5 mL) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (80 mg, 48%). The product was characterized by $^1$H NMR (400 MHz) in $CDCl_3$.

1-(2-{[(4-fluorophenyl)methyl]oxy}ethyl)-4-[hydroxy(diphenyl)methyl]-1-azoniabicyclo[2.2.2]octane bromide 1-Azabicyclo[2.2.2]oct-4-yl(diphenyl)methanol (30 mg, 0.102 mmol) was added to a solution of 1-{[(2-bromoethyl)oxy]methyl}-4-fluorobenzene (33 mg, 0.143 mmol) in 2:3

CH$_3$CN/CHCl$_3$ (3 mL), and the reaction was heated at 60° C. for 96 h. The reaction was concentrated, and the crude product was washed with EtOAc (3×1 mL). The product was dried under high vacuum to give the title compound (9 mg, 16%). LC/MS ESI R$_T$ 1.89 min M$^+$ 446

Example 78

Preparation of 1-(2-{[(4-chlorophenyl)methyl]oxy}ethyl)-4-[hydroxy(diphenyl)methyl]-1-azoniabicyclo[2.2.2]octane bromide 2-{[(4-chlorophenyl)methyl]oxy}ethanol Ethylene glycol (0.084 mL, 1.5 mmol) was added to NaH (38 mg, 1.52 mmol, 95% in oil) in THF (3 mL). 1-(Bromomethyl)-4-chlorobenzene (310 mg, 1.5 mmol) was added to the reaction, and the residual 1-(bromomethyl)-4-chlorobenzene was transferred to the reaction tube with additional THF (1 mL). (Bu)$_4$NI (55 mg, 0.15 mmol) was then added, and the reaction was heated at 60° C. for 18 h and then rt for 4 h. H$_2$O (2 mL) and EtOAc (2 mL) were added, and the layers were separated via pipette. The aqueous layer was extracted with EtOAc (1×1 mL), and the combined organic layers were concentrated. The crude product was purified on a SPE cartridge (5 g silica) eluting with the following 10 mL fractions: 30% EtOAc/hexanes (fractions 1,2), 50% EtOAc/hexanes (fraction 3), and 75% EtOAc/hexanes (fraction 4) to give the title compound (129 mg, 46%). The product was characterized by $^1$H NMR (400 MHz) in CDCl$_3$.

1-{[(2-bromoethyl)oxy]methyl}-4-chlorobenzene

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution of 2-{[(4-chlorophenyl)methyl]oxy}ethanol (129 mg, 0.691 mmol) in DCM (1.5 mL) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (98 mg, 57%). The product was characterized by $^1$H NMR (400 MHz) in CDCl$_3$.

1-(2-{[(4-chlorophenyl)methyl]oxy}ethyl)-4-[hydroxy(diphenyl)methyl]-1-azoniabicyclo[2.2.2]octane bromide 1-Azabicyclo[2.2.2]oct-4-yl(diphenyl)methanol (30 mg, 0.102 mmol) was added to a solution of 1-{[(2-bromoethyl)oxy]methyl}-4-chlorobenzene (36 mg, 0.143 mmol) in 2:3 CH$_3$CN/CHCl$_3$ (3 mL), and the reaction was heated at 60° C. for 96 h. The reaction was concentrated, and the crude product was washed with EtOAc (3×1 mL). The product was dried under high vacuum to give the title compound (17.4 mg, 32%). LC/MS ESI R$_T$ 2.09 min M$^+$ 462

Example 79

Preparation of 1-(2-{[(4-bromophenyl)methyl]oxy}ethyl)-4-[hydroxy(diphenyl)methyl]-1-azoniabicyclo[2.2.2]octane bromide 2-{[(4-bromophenyl)methyl]oxy}ethanol Ethylene glycol (0.084 mL, 1.5 mmol) was added to NaH (38 mg, 1.52 mmol, 95% in oil) in THF (3 mL). 1-Bromo-4-(bromomethyl)benzene (370 mg, 1.5 mmol) was added to the reaction, and the residual 1-bromo-4-(bromomethyl)benzene was transferred to the reaction tube with additional THF (1 mL). (Bu)$_4$NI (55 mg, 0.15 mmol) was then added, and the reaction was heated at 60° C. for 18 h and then rt for 4 h. H$_2$O (2 mL) and EtOAc (2 mL) were added, and the layers were separated via pipette. The aqueous layer was extracted with EtOAc (1×1 mL), and the combined organic layers were concentrated. The crude product was purified on a SPE cartridge (5 g silica) eluting with the following 10 mL fractions: 30% EtOAc/hexanes (fractions 1,2), 50% EtOAc/hexanes (fraction 3), and 75% EtOAc/hexanes (fraction 4) to give the title compound (139 mg, 40%). The product was characterized by $^1$H NMR (400 MHz) in CDCl$_3$.

1-bromo-4-{[2-bromoethyl)oxy]methyl}benzene

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution of 2-{[(4-bromophenyl)methyl]oxy}ethanol (139 mg, 0.601 mmol) in DCM (1.5 ML) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (87 mg, 49%). The product was characterized by $^1$H NMR (400 MHz) in CDCl$_3$.

1-(2-{[(4-bromophenyl)methyl]oxy}ethyl)-4-[hydroxy(diphenyl)methyl]-1-azoniabicyclo[2.2.2]octane bromide 1-Azabicyclo[2.2.2]oct-4-yl(diphenyl)methanol (30 mg, 0.102 mmol) was added to a solution of 1-bromo-4-{[(2-bromoethyl)oxy]methyl}benzene (42 mg, 0.143 mmol) in 2:3 CH$_3$CN/CHCl$_3$ (3 mL), and the reaction was heated at 60° C. for 96 h. The reaction was concentrated, and the crude product was washed with EtOAc (3×1 mL). The product was dried under high vacuum to give the title compound (19.4 mg, 32%). LC/MS ESI R$_T$ 2.07 min M$^+$ 506

Example 80

Preparation of 1-(2-{[(4-cyanophenyl)methyl]oxy}ethyl)-4-[hydroxy(diphenyl)methyl]-1-azoniabicyclo[2.2.2]octane bromide 4-{[(2-hydroxyethyl)oxy]methyl}benzonitrile Ethylene glycol (0.084 mL, 1.5 mmol) was added to NaH (38 mg, 1.52 mmol, 95% in oil) in THF (3 mL). 4-(Bromomethyl)benzonitrile (290 mg, 1.5 mmol) was added to the reaction, and the residual 4-(bromomethyl)benzonitrile was transferred to the reaction tube with additional THF (1 mL). (Bu)$_4$NI (55 mg, 0.15 mmol) was then added, and the reaction was heated at 60° C. for 18 h and then rt for 4 h. H$_2$O (2 mL) and EtOAc (2 mL) were added, and the layers were separated via pipette. The aqueous layer was extracted with EtOAc (1×1 mL), and the combined organic layers were concentrated. The crude product was purified on a SPE cartridge (5 g silica) eluting with the following 10 mL fractions: 10% EtOAc/hexanes (fractions 1,2), 30% EtOAc/hexanes (fractions 3,4), 50% EtOAc/hexanes (fractions 5-7), and 75% EtOAc/hexanes (fraction 8) to give the title compound (95 mg, 36%). The product was characterized by 1H NMR (400 MHz) in CDCl$_3$.

4-{[(2-bromoethyl)oxy]methyl}benzonitrile

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution of 4-{[(2-hydroxyethyl)oxy]methyl}benzonitrile (95 mg, 0.536 mmol) in DCM (1.5 mL) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (60 mg, 47%). The product was characterized by $^1$H NMR (400 MHz) in CDCl$_3$.

1-(2-{[(4-cyanophenyl)methyl]oxy}ethyl)-4-[hydroxy(diphenyl)methyl]-1-azoniabicyclo[2.2.2]octane bromide 1-Azabicyclo[2.2.2]oct-4-yl(diphenyl)methanol (30 mg, 0.102 mmol) was added to a solution of 4-{[(2-bromoethyl)oxy]methyl}benzonitrile (34 mg, 0.143 mmol) in 2:3 CH$_3$CN/CHCl$_3$ (3 mL), and the reaction was heated at 60° C. for 96 h. The reaction was concentrated, and the crude product was washed with EtOAc (3×1 mL). The product was dried under high vacuum to give the title compound (40 mg, 74%). LC/MS ESI R$_T$ 1.82 min M$^+$ 453

Example 81

Preparation of 4-[hydroxy(diphenyl)methyl]-1-{2-[(2-naphthalenylmethyl)oxy]ethyl}-1-azoniabicyclo[2.2.2]octane bromide

2-[2-naphthalenylmethyl)oxy]ethanol

Ethylene glycol (0.084 mL, 1.5 mmol) was added to NaH (38 mg, 1.52 mmol, 95% in oil) in THF (3 mL). 2-(Bromomethyl)naphthalene (330 mg, 1.5 mmol) was added to the reaction, and the residual 2-(bromomethyl)naphthalene was transferred to the reaction tube with additional THF (1 mL). (Bu)$_4$NI (55 mg, 0.15 mmol) was then added, and the reaction was heated at 60° C. for 18 h and then rt for 4 h. H$_2$O (2 mL) and EtOAc (2 mL) were added, and the layers were separated via pipette. The aqueous layer was extracted with EtOAc (1×1 mL), and the combined organic layers were concentrated. The crude product was purified on a SPE cartridge (5 g silica) eluting with the following 10 mL fractions: 30% EtOAc/hexanes (fractions 1,2), 50% EtOAc/hexanes (fraction 3), and 75% EtOAc/hexanes (fraction 4) to give the title compound (101 mg, 33%). The product was characterized by $^1$H NMR (400 MHz) in CDCl$_3$.

2-{[(2-bromoethyl)oxy]methyl}naphthalene

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution 2-[(2-naphthalenylmethyl)oxy]ethanol (101 mg, 0.499 mmol) in DCM (1.5 mL) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (57 mg, 43%). The product was characterized by $^1$H NMR (400 MHz) in CDCl$_3$.

4-[hydroxy(diphenyl)methyl]-1-{2-[2-naphthalenylmethyl)oxy]ethyl}-1-azoniabicyclo[2.2.2]octane bromide 1-Azabicyclo[2.2.2]oct-4-yl(diphenyl)methanol (30 mg, 0.102 mmol) was added to a solution of 2-{[(2-bromoethyl)oxy]methyl}naphthalene (38 mg, 0.143 mmol) in 2:3 CH$_3$CN/CHCl$_3$ (3 mL), and the reaction was heated at 60° C. for 96 h. The reaction was concentrated, and the crude product was washed with EtOAc (3×1 mL). The product was dried under high vacuum to give the title compound (48.1 mg, 84%). LC/MS ESI R$_T$ 2.04 min M$^+$ 478

Example 82

Preparation of 1-(2-{[(3-fluorophenyl)methyl]oxy}ethyl)-4-[hydroxy(diphenyl)methyl]-1-azoniabicyclo[2.2.2]octane bromide

2-{[3-fluorophenyl)methyl]oxy}ethanol

Ethylene glycol (0.1 mL, 1.79 mmol) was added to NaH (46 mg, 1.81 mmol, 95% in oil) in THF (5 mL). 1-(Bromomethyl)-3-fluorobenzene (0.22 mL, 1.79 mmol) was added to the reaction, and the reaction was heated at 60° C. for 5 days. H$_2$O (2 mL) and EtOAc (2 mL) were added, and the layers were separated via pipette. The aqueous layer was extracted with EtOAc (3×1 mL), and the combined organic layers were washed with saturated NaCl (1×2 mL), dried (Na$_2$SO$_4$), and concentrated. The crude product was purified on a SPE cartridge (5 g silica) eluting with the following 10 mL fractions: 30% EtOAc/hexanes (fractions 1,2), 50% EtOAc/hexanes (fraction 3), and 75% EtOAc/hexanes (fraction 4) to give the title compound (76.2 mg, 25%). The product was characterized by $^1$H NMR (400 MHz) in CDCl$_3$.

1-{[(2-bromoethyl)oxy]methyl}-3-fluorobenzene

N-bromosuccinimide (146 mg, 0.820 mmol) was added to resin-bound triphenylphosphine (274 mg, 0.822 mEquiv, Fluka) and 2-{[(3-fluorophenyl)methyl]oxy}ethanol (70 mg, 0.411 mmol) in DCM (4 mL). The reaction vial was sealed with a Teflon-lined cap, wrapped in aluminum foil, and shaken at rt for 17 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (75 mg, 78%). The product was characterized by $^1$H NMR (400 MHz) in CDCl$_3$.

1-(2-{[(3-fluorophenyl)methyl]oxy}ethyl)-4-[hydroxy(diphenyl)methyl]-1-azoniabicyclo[2.2.2]octane bromide 1-Azabicyclo[2.2.2]oct-4-yl(diphenyl)methanol (94 mg, 0.321 mmol) was added to a solution of 1-{[(2-bromoethyl)oxy]methyl}-3-fluorobenzene (75 mg, 0.321 mmol) in 2:3 CH$_3$CN/CHCl$_3$ (4 mL), and the reaction was heated at 60° C. for 3 days. The reaction was concentrated under reduced pressure, and the crude product was washed with EtOAc (3×2 mL). The product was dried under high vacuum to give the title compound (50 mg, 30%). LC/MS ESI R$_T$ 1.95 min M$^+$ 446

Example 83

Preparation of 4-[hydroxy(diphenyl)methyl]-1-{2-[(1-methyl-1-phenylethyl)oxy]ethyl}-1-azoniabicyclo[2.2.2]octane bromide

2-[(1-methyl-1-phenylethyl)oxy]ethanol

A catalytic amount of either p-toluene sulfonic acid•H$_2$O or Bio-Rad SCX resin (analytical grade, 5.1 meq/g, AG 50W-X8) was added to □-methylstyrene (0.5 mL, 3.85 mmol) and ethylene glycol (0.21 mL, 3.85 mmol), and the reaction was stirred at rt for 5 days. The reaction mixture was loaded directly onto a SPE cartridge (10 g silica) and eluted with the following 10 mL fractions: 10% EtOAc/hexanes (fractions 1,2), 30% EtOAc/hexanes (fractions 3,4), and 50% EtOAc/hexanes (fractions 5,6) to give the title compound (30.5 mg, 4%) for both conditions. The product was characterized by $^1$H NMR (400 MHz) in CDCl$_3$.

{1-[(2-bromoethyl)oxy]-1-methylethyl}benzene

N-bromosuccinimide (119 mg, 0.666 mmol) was added to resin-bound triphenylphosphine (222 mg, 0.666 mEquiv, Fluka) and 2-[(1-methyl-1-phenylethyl)oxy]ethanol (60 mg, 0.333 mmol) in DCM (4 mL). The reaction vial was sealed with a Teflon-lined cap, wrapped in aluminum foil, and shaken at rt for 17 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (34 mg, 42%). The product was characterized by $^1$H NMR (400 MHz) in CDCl$_3$.

4-[hydroxy(diphenyl)methyl]-1-{2-[(1-methyl-1-phenylethyl)oxy]ethyl}-1-azoniabicyclo[2.2.2]octane bromide 1-Azabicyclo[2.2.2]oct-4-yl(diphenyl)methanol (41 mg, 0.14 mmol) was added to a solution of {1-[(2-bromoethyl)oxy]-1-methylethyl}benzene (34 mg, 0.14 mmol) in 2:3 CH$_3$CN/CHCl$_3$ (3 mL), and the reaction was heated at 60° C. for 3 days. The reaction was concentrated under reduced pressure, and the crude product was washed with EtOAc (3×1 mL). The residue was taken up in 2.5 mL of DMSO and purified by preparatory HPLC (without TFA) to give the title compound (18 mg, 24%). LC/MS ESI R$_T$ 2.09 min M$^+$ 456

Example 84

Preparation of 4-[hydroxy(diphenyl)methyl]-1-{2-[(phenylmethyl)oxy]ethyl}-1-azoniabicyclo[2.2.2]octane bromide Method A: 1-Azabicyclo[2.2.2]oct-4-yl(diphenyl)methanol (0.020 g, 0.068 mmol) was diluted in CHCl$_3$ (1.8 mL) and dispensed directly into a 1 dram vial containing 2-bromoethyl phenylmethyl ether (0.022 g, 0.102 mmol). CH$_3$CN (1.2 mL) was added; the vial was fitted with a stirring bar and capped. The reaction was stirred and heated at 60° C. for 24 h. The contents of the vial were transferred (after removal of stirring bar) into a polypropylene tube and concentrated under Nitrogen. The crude product was collected on a polypropylene tube frit. Excess bromide was removed by washing the crude product with EtOAc (5×2 mL) and Hexane (5×2 mL). The product was then dried under vacuum to give the title compound (0.008 g, 23.8%).

Method B: To a solution of 1-azabicyclo[2.2.2]oct-4-yl (diphenyl)methanol (3.30 g, 11.2 mmol) in 2 CH$_3$CN/3 CHCl$_3$ (200 mL) was added 2-bromoethyl phenylmethyl ether (2.31 mL, 14.6 mmol). The solution was stirred at 60° C. for 16 h. The reaction was cooled down to room temperature and concentrated. EtOAc (200 mL) was added to the solid, and the mixture was allowed to stir for 1 hour then filtered. The resulting solid was taken up in MeOH (125 mL) and heated to 60° C. The solution was filtered hot, and then cooled back to room temperature. The reaction was concentrated to a low volume of MeOH (~20 mL) and filtered. Water (75 mL) was then added and the resulting mixture was heated at 55° C. with brisk stirring for 40 min. After cooling to room temperature, the solid was filtered off, washed with water (20 mL) and dried in a vacuum oven at 45° C. for 16 hours to give the title compound (2.47 g, 43.3%). EI-MS m/z 428(M$^+$) Rt (1.90 min) $^1$H NMR (DMSO-d$_6$) δ 7.56 (d, 4H, J=1.2), 7.28 (m, 11H), 5.95 (s, 1H), 4.50 (s, 2H), 3.81 (d, 2H, J=4.0), 3.48 (t, 6H, J=7.2), 3.38 (d, 2H, J=4.0), 2.01 (t, 6H, J=7.2); Elemental analysis (C$_{29}$H$_{34}$NO$_2$Br) C, H, N: calculated, 68.50, 6.74, 2.75. found, 68.28, 6.68, 2.73.

The following examples in Table 1 were prepared according to the procedure outlined in Example 84 method A.

TABLE 1

| Example | R1 | MS [M+] | R$_t$(min) |
|---|---|---|---|
| 85 | (benzyl-C(CH$_3$)$_2$-) | 384 | 1.64 |
| 86 | (2-naphthylmethyl-C(CH$_3$)$_2$-) | 434 | 1.97 |

TABLE 1-continued
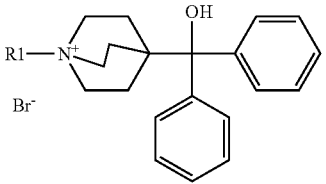
| Example | R1 | MS [M+] | R_r(min) |
|---|---|---|---|
| 87 | 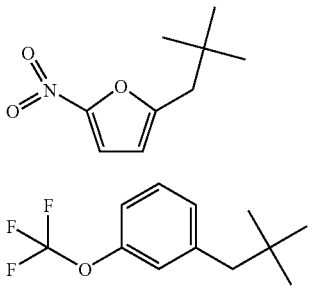 | 419 | 1.51 |
| 88 | 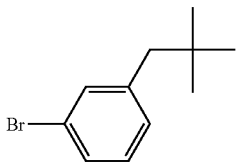 | 468 | 2.02 |
| 89 | 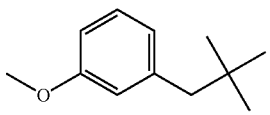 | 463 | 1.77 |
| 90 | 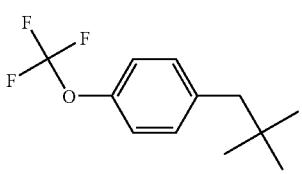 | 414 | 1.84 |
| 91 | 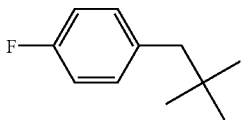 | 468 | 1.96 |
| 92 | 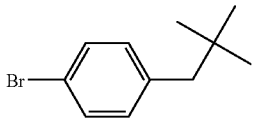 | 402 | 1.68 |
| 93 | 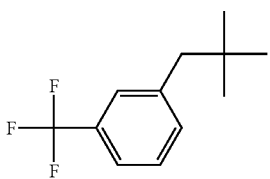 | 463 | 1.82 |
| 94 | 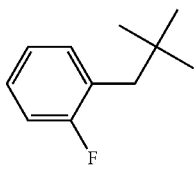 | 452 | 1.93 |
| 95 | | 402 | 1.55 |

TABLE 1-continued

| Example | R1 | MS [M+] | R$_t$(min) |
|---|---|---|---|
| 96 | 4-(trifluoromethyl)benzyl-neopentyl | 452 | 1.97 |
| 97 | cyclohexyl-propyl-neopentyl | 418 | 2.00 |
| 98 | 4-methylbenzyl-neopentyl | 398 | 1.72 |
| 99 | 2-(3-methylpyrazol-1-yl)ethyl-neopentyl | 402 | 1.60 |
| 100 | 3-fluorobenzyl-neopentyl | 402 | 1.63 |
| 101 | 3,4-dichlorobenzyl-neopentyl | 453 | 1.92 |
| 102 | 2-fluoro-3-methylbenzyl-neopentyl | 416 | 1.87 |
| 103 | 4-cyanobenzyl-neopentyl | 409 | 1.60 |

TABLE 1-continued
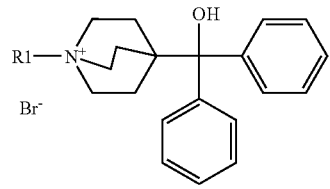
| Example | R1 | MS [M+] | R_t(min) |
|---|---|---|---|
| 104 | 4-tert-butylbenzyl neopentyl | 440 | 2.07 |
| 105 | 3-cyanobenzyl neopentyl | 409 | 1.55 |
| 106 | 2,4-difluorobenzyl neopentyl | 420 | 1.90 |
| 107 | 2,3-difluorobenzyl neopentyl | 420 | 1.78 |
| 108 | N-Cbz-4-piperidinyl neopentyl | 525 | 1.67 |
| 109 | 4-nitrobenzyl neopentyl | 429 | 1.57 |
| 110 | 3,4-difluorobenzyl neopentyl | 420 | 1.64 |
| 111 | 2,6-difluorobenzyl neopentyl | 420 | 1.67 |

Example 112

Preparation of 1-[2-(1-benzofuran-2-yl)-2-oxoethyl]-4-[hydroxy(diphenyl)methyl]-1-azoniabicyclo[2.2.2]octane bromide 1-azabicyclo[2.2.2]oct-4-yl(diphenyl)methanol (0.022 g, 0.075 mmol) was diluted in CHCl$_3$ (1.8 mL) and dispensed directly into a 1 dram vial containing 1-(1-benzofuran-2-yl)-2-bromoethanone (0.027 g, 0.112 mmol). Added CH$_3$CN (1.2 mL), the vial was fitted with stirring bar and capped. The reaction was stirred and heated at 60° C. for 24 h and then concentrated under vacuum to give a white solid. This residue was dissolved in DMSO and purified by preparatory HPLC (without TFA) to give the title compound (0.022 g, 57.4%). LC/MS ESI R$_T$ 1.98 min, M$^+$ 452

The following examples in Table 2 were prepared according to the procedure outlined in Example 112.

TABLE 2

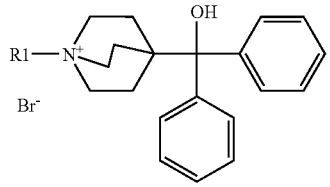

| Example | R1 | MS [M+] | R$_t$(min) |
|---|---|---|---|
| 113 | (indol-3-yl)CH$_2$CH$_2$C(CH$_3$)$_2$– | 437 | 1.96 |
| 114 | PhNHC(O)CH(CH$_3$)C(CH$_3$)$_3$ | 441 | 1.92 |
| 115 | (2,4-Cl$_2$-C$_6$H$_3$)NHC(O)NHCH$_2$CH$_2$C(CH$_3$)$_3$ | 525 | 2.11 |
| 116 | (4-Ph-C$_6$H$_4$)C(O)CH$_2$C(CH$_3$)$_3$ | 488 | 2.31 |
| 117 | (4-pentyl-C$_6$H$_4$)C(O)CH$_2$C(CH$_3$)$_3$ | 482 | 2.46 |
| 118 | (2,4-Cl$_2$-C$_6$H$_3$)C(O)NHCH$_2$CH$_2$C(CH$_3$)$_3$ | 510 | 1.95 |
| 119 | (naphth-2-yl)C(O)CH$_2$C(CH$_3$)$_3$ | 462 | 2.03 |

TABLE 2-continued

[Structure: R1—N⁺(bicyclic) with Br⁻ counterion, bearing C(OH)(phenyl)(phenyl) group]

| Example | R1 | MS [M+] | R$_t$(min) |
|---|---|---|---|
| 120 | [benzoyl-O-CH$_2$CH$_2$-C(CH$_3$)$_3$] | 442 | 1.95 |
| 121 | [CH$_3$-SO$_2$-NH-CH$_2$CH$_2$-C(CH$_3$)$_3$] | 429 | 1.33 |
| 122 | [2-phenoxy-pyridine-3-C(O)NH-CH$_2$CH$_2$-C(CH$_3$)$_3$] | 534 | 1.92 |

Abbreviations

Ar Argon
DCM Dichloromethane
DMF Dimethylformanmide
DMSO Dimethylsulfoxide
EI/ESI Electrospray ionization
HPLC High pressure liquid chromatography
LC Liquid chromatography
LDA Lithium Diisopropyl Amide
MS Mass spectrometry
NMR Nuclear magnetic resonance
Rt Retention time
rt room temperature
SPE Solid phase extraction
TEA Triethylamine
TFA Trifluoroacetic acid
THF Tetrahydrofuran

BIOLOGICAL EXAMPLES

The inhibitory effects of compounds at the M$_3$ mAChR of the present invention are determined by the following in vitro and in vivo functional assays:

Analysis of Inhibition of Receptor Activation by Calcium Mobilization:

Stimulation of mAChRs expressed on CHO cells were analyzed by monitoring receptor-activated calcium mobilization as previously described (H. M. Sarau et al, 1999. *Mol. Pharmacol.* 56, 657-663). CHO cells stably expressing M$_3$ mAChRs were plated in 96 well black wall/clear bottom plates. After 18 to 24 hours, media was aspirated and replaced with 100 µl of load media (EMEM with Earl's salts, 0.1% RIA-grade BSA (Sigma, St. Louis Mo.), and 4 µM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 µl of assay buffer (0.1% gelatin (Sigma), 120 mM NaCl, 4.6 mM KCl, 1 mM KH$_2$ PO$_4$, 25 mM NaH CO$_3$, 1.0 mM CaCl$_2$, 1.1 mM MgCl$_2$, 11 mM glucose, 20 mM HEPES (pH 7.4)). 50 µl of compound ($1\times10^{-11}$–$1\times10^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 µl of acetylcholine (0.1-10 nM final), prepared in buffer containing 0.1% BSA, at a rate of 50 µl/sec. Calcium mobilization, monitored as change in cytosolic calcium concentration, was measured as change in 566 nm emission intensity. The change in emission intensity is directly related to cytosolic calcium levels. The emitted fluorescence from all 96 wells is measured simultaneously using a cooled CCD camera. Data points are collected every second. This data was then plotting and analyzed using GraphPad PRISM software.

Methacholine-Induced Bronchoconstriction—Potency and Duration of Action

Airway responsiveness to methacholine was determined in awake, unrestrained Balb C mice (n=6 each group). Barometric plethysmography was used to measure enhanced pause (Penh), a unitless measure that has been shown to correlate with the changes in airway resistance that occur during bronchial challenge with methacholine (2). Mice were pre-treated with 50 µl of compound (0.003-10 µg/mouse) in 50 µl of vehicle (10% DMSO) intranasally (i.n.) and were then placed in the plethysmography chamber a given amount of time following drug administration (15 min-96 h). For potency determination, a dose response to a given drug was performed, and all measurements were taken 15 min following i.n. drug administration. For duration of action determination, measurements were taken anywhere from 15 min to 96 hours following i.n. drug administration.

Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software. This experiment allows the determination of duration of activity of the administered compound.

The present compounds are useful for treating a variety of indications, including but not limited to respiratory-tract disorders such as chronic obstructive lung disease, chronic bronchitis, asthma, chronic respiratory obstruction, pulmonary fibrosis, pulmonary emphysema, and allergic rhinitis.

Muscarinic Receptor Radioligand Binding Assays

Radioligand binding studies using 0.5 nM[$^3$H]-N-methyl scopolamine (NMS) in a SPA format is used to assess binding of muscarinic antagonists to $M_1$, $M_2$, $M_3$, $M_4$ and $M_5$ muscarinic acetylcholine receptors. In a 96-well plate, the SPA beads are pre-incubated with receptor-containing membrane for 30 min at 4° C. Then 50 mM HEPES and the test compound are added and incubated at room temperature (shaking) for 2 hours. The beads are then spun down and counted using a scintillation counter.

Evaluation of Potency and Duration of Action in Isolated Guinea Pig Trachea

Tracheae were removed from adult male Hartely guinea pigs (Charles River, Raleigh, N.C.; 400-600 grams) and placed into modified Krebs-Henseleit solution. Composition of the solution was (mM): NaCl 113.0, KCl 4.8, $CaCl_2$ 2.5, $KH_2PO_4$ 1.2, $MgSO_4$ 1.2, $NaHCO_3$ 25.0 and dextrose 11.0. which was gassed with 95% $O_2$: 5% $CO_2$ and maintained at 37° C. Each trachea was cleaned of adherent tissue and opened lengthwise. Epithelium was removed by gently rubbing the luminal surface with a cotton-tipped applicator. Individual strips were cut, approximately 2 cartilage rings in width, and suspended via silk suture in 10-ml water-jacketed organ baths containing Krebs-Henseleit solution and connected to Grass FT03C force-displacement transducers. Mechanical responses were recorded isometrically by MP100WS/Acknowledge data acquisition system (BIOPAC Systems, Goleta, Calif., www.biopac.com) run on Apple G4 computers. The tissues were equilibrated under a resting tension of 1.5 g, determined to be optimal by length-tension evaluation, and washed with Krebs-Henseleit solution every 15 minutes for one hour. After the equilibration period pulmonary tissues were contracted with 10 uM carbachol until reaching plateau, which served as a reference contraction for data analysis. Tissues were then rinsed every 15 minutes over 1 hour until reaching baseline tone. The preparations were then left for at least 30 minutes before the start of the experiment.

Concentration-response curves were obtained by a cumulative addition of carbachol in half-log increments (Van Rossum, 1963, Arch. Int. Pharmacodyn., 143:299), initiated at 1 nM. Each concentration was left in contact with the preparation until the response plateaued before the addition of the subsequent carbachol concentration. Paired tissues were exposed to mAChR antagonist compounds or vehicle for 30 min before carbachol cumulative concentration-response curves were generated. All data is given as mean ± standard error of the mean (s.e.m.) with n being the number of different animals.

For superfusion (duration of action) studies, the tissues were continuously superfused with Krebs-Henseleit solution at 2 ml/min for the duration of the experiment. Stock solutions of agonist and antagonist were infused (0.02 ml/min) via 22-guage needle inserted into the superfusion tubing. Mechanical responses were recorded isometrically using a commercially-available data acquisition system (MP100WS/Acknowledge; BIOPAC Systems, Goleta, Calif., www.biopac.com) interfaced with a Macintosh G4 computer (Apple, Cupertino, Calif. www.apple.com). The tissues were suspended under an optimal resting tension of 1.5 g. After a 60 min equilibration period, the tissues were contracted with carbachol (1 uM) for the duration of the experiment. Upon reaching a sustained contraction isoproterenol (10 uM) was administered to maximally relax the tissue, and this change served as a reference. Isoproterenol exposure was halted and the carbachol-induced tension allowed to recover. Muscarinic receptor antagonists infused at a single concentration per tissue until a sustained level of inhibition was attained. The compound was then removed and, once again, the carbachol-induced tension was allowed to recover.

The following parameters were determined for each concentration of antagonist, and expressed as the mean ± S.E.M. for n individual animals. Inhibition of the carbachol-induced contraction was expressed as a percent of the reference response (isoproterenol) and the time required to reach one-half of this relaxation was measured (onset of response). The tension recovery following removal of the compound was determined as was the time required to reach one-half of the maximum tension recovery (offset of response). At 60 and 180 minutes after removal of the antagonist the remaining level of inhibition was determined and expressed as a percent of the isoproterenol reference.

Antagonist concentration-response curves were obtained by plotting the maximal relaxation data at 0, 60 and 180-min following antagonist withdrawal. Recovery, termed shift, was calculated from the ratio of the 0-min inhibition curve $IC_{50}$ and the concentration of compound yielding a similar tension recovery at 60 and 180 minutes.

Halftimes for onset and offset of response were plotted vs. corresponding concentration and the data were fit with non-linear regression. These values were extrapolated at the $IC_{50}$ (determined from the inhibition concentration-response curve) and designated $Ot_{50}$ (time required, at the $IC_{50}$ concentration, to reach half of the onset response) and Rt50 (time required, at the $IC_{50}$ concentration, to reach half of the recovery response).

Formulation-Administration

Accordingly, the present invention further provides a pharmaceutical formulation comprising a compound of formula (I), or a pharmaceutically acceptable salt, solvate, or physiologically functional derivative (e.g., salts and esters) thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

Compounds of formula (I) will be administered via inhalation via the mouth or nose.

Dry powder compositions for topical delivery to the lung by inhalation may, for example, be presented in capsules and cartridges of for example gelatine, or blisters of for example laminated aluminum foil, for use in an inhaler or insufflator.

Powder blend formulations generally contain a powder mix for inhalation of the compound of the invention and a suitable powder base (carrier/diluent/excipient substance) such as mono-, di- or poly-saccharides (e.g., lactose or starch), organic or inorganic salts (e.g., calcium chloride, calcium phosphate or sodium chloride), polyalcohols (e.g., mannitol), or mixtures thereof, alternatively with one or more additional materials, such additives included in the blend formulation to improve chemical and/or physical stability or performance of the formulation, as discussed below, or mixtures thereof. Use of lactose is preferred. Each capsule or cartridge may generally contain between 20 µg-10 mg of the compound of formula (I) optionally in combination with another therapeutically active ingredient. Alternatively, the compound of the invention may be presented without excipients, or may be formed into particles comprising the compound, optionally other therapeutically active materials, and excipient materials, such as by co-precipitation or coating.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant as an inhaler having a reservoir form pack suitable for comprising multiple (un-metered doses) of medicament in dry powder form and including means for metering medicament dose from the reservoir to a delivery position. The metering means may for example comprise a metering cup or perforated plate, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disk-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Spray compositions for topical delivery to the lung by inhalation may for example be formulated as aqueous solutions or suspensions or as aerosols delivered from pressurized packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum aerodynamic particle size for inhalation into the bronchial system for localized delivery to the lung is usually 1-10 µm, preferably 2-5 µm. The optimum aerodynamic particle size for inhalation into the alveolar region for achieving systemic delivery to the lung is approximately 0.5-3 µm, preferably 1-3 µm. Particles having an aerodynamic size above 20 µm are generally too large when inhaled to reach the small airways. Average aerodynamic particle size of a formulation may measured by, for example cascade impaction. Average geometric particle size may be measured, for example by laser diffraction, optical means.

To achieve a desired particle size, the particles of the active ingredient as produced may be size reduced by conventional means eg by controlled crystallization, micronisation or nanomilling The desired fraction may be separated out by air classification. Alternatively, particles of the desired size may be directly produced, for example by spray drying, controlling the spray drying parameters to generate particles of the desired size range. Preferably, the particles will be crystalline, although amorphous material may also be employed where desirable. When an excipient such as lactose is employed, generally, the particle size of the excipient will be much greater than the inhaled medicament within the present invention, such that the "coarse" carrier is non-respirable. When the excipient is lactose it will typically be present as milled lactose, wherein not more than 85% of lactose particles will have a MMD of 60-90 μm and not less than 15% will have a MMD of less than 15 μm. Additive materials in a dry powder blend in addition to the carrier may be either respirable, i.e., aerodynamically less than 10 microns, or non-respirable, i.e., aerodynamically greater than 10 microns.

Suitable additive materials which may be employed include amino acids, such as leucine; water soluble or water insoluble, natural or synthetic surfactants, such as lecithin (e.g., soya lecithin) and solid state fatty acids (e.g., lauric, palmitic, and stearic acids) and derivatives thereof (such as salts and esters); phosphatidylcholines; sugar esters. Additive materials may also include colorants, taste masking agents (e.g., saccharine), anti-static-agents, lubricants (see, for example, Published PCT Patent Appl. No. WO 87/905213, the teachings of which are incorporated by reference herein), chemical stabilizers, buffers, preservatives, absorption enhancers, and other materials known to those of ordinary skill.

Sustained release coating materials (e.g., stearic acid or polymers, e.g. polyvinyl pyrolidone, polylactic acid) may also be employed on active material or active material containing particles (see, for example, U.S. Pat. No. 3,634,582, GB 1,230,087, GB 1,381,872, the teachings of which are incorporated by reference herein).

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as herein before recited, or an appropriate fraction thereof, of the active ingredient.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I)

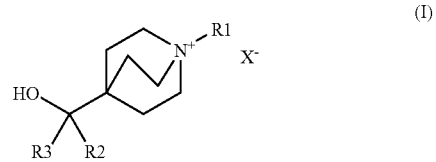

wherein:
R1 is

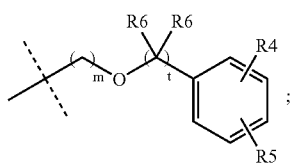

R2 and R3 are independently selected from the group consisting of

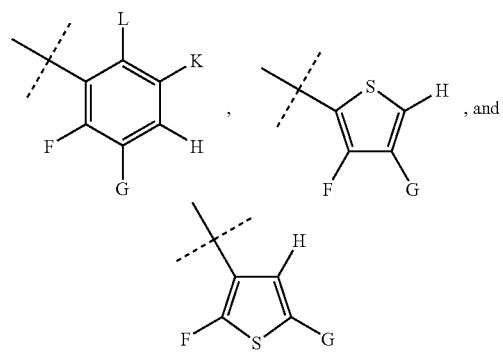

F, G, H, K and L are independently selected from the group consisting of hydrogen, halogen, $C_{1-4}$ alkyl, halosubstituted $C_{1-4}$ alkyl, hydroxy substituted alkyl, and $C_{1-4}$alkoxy;

$R_4$ and $R_5$ are independently selected from the group consisting of hydrogen, halogen, C1-4 alkyl, aryl, C1-4 alkyl aryl, cyano, nitro, (CR7R7)pORb and (CR7R7)pNRbRb;

R6 is selected from the group consisting of hydrogen, C1-4 alkyl;

m is an integer having a value of 1 to 15;

t is 0 or an integer having a value of 1 to 5;

p is 0 or an integer having a value of 1 to 4;

Rb is selected from the group consisting of hydrogen, C1-4 alkyl, aryl and C1-4 alkyl aryl;

R7 is selected from the group consisting of hydrogen, C1-4 alkyl, halosubstituted C1-4 alkyl, and hydroxy substituted C1-4 alkyl; and $X^-$ is a pharmaceutically acceptable anion.

2. A compound according to claim 1
wherein
m is an integer having a value of 1 to 5;
t is 0, 1 or 2;
p is 0, 1 or 2;

R6 is selected from the group consisting of hydrogen and C1-4 alkyl;

Rb is selected from the group consisting of hydrogen, C1-4 alkyl and aryl C1-4 alkyl;

R7 is selected from the group consisting of hydrogen and C1-4 alkyl; and

X⁻ is a pharmaceutically acceptable anion selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate and p-tlouenesulfonate.

3. A pharmaceutical composition comprising a compound according to claim 1 and a pharmaceutically acceptable carrier thereof.

4. The compound according to claim 1 wherein X⁻ is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

5. The compound according to claim 1 wherein R2 and R3 are both independently selected from

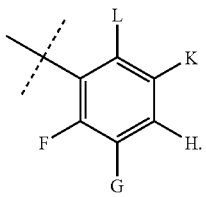

6. The compound according to claim 5 wherein F, G, H, K and L are hydrogen.

7. The compound according to claim 1 wherein R2 and R3 are both independently selected from

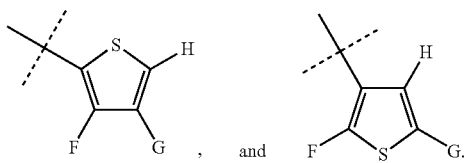

8. The compound according to claim 7 wherein F, G and H are hydrogen.

9. The compound according to claim 2 wherein R2 and R3 are both independently selected from

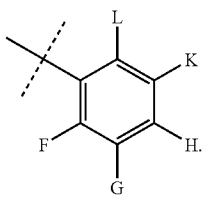

10. The compound according to claim 9 wherein F, G, H, K and L are hydrogen.

11. The compound according to claim 2 wherein R2 and R3 are both independently selected from

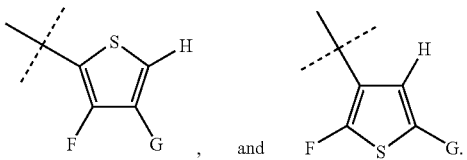

12. The compound according to claim 11 wherein F, G and H are hydrogen.

13. The compound according to claim 2 wherein F, G, H, K and L are hydrogen.

14. The compound according to claim 1 wherein R4 and R5 are both hydrogen.

15. The compound according to claim 2 wherein R4 and R5 are both hydrogen.

16. The compound according to claim 10 wherein R4 and R5 are both hydrogen.

17. The compound according to claim 1 wherein m is 2, 3 or 4.

18. The compound according to claim 2 wherein m is 2, 3 or 4.

19. The compound according to claim 10 wherein m is 2, 3 or 4.

20. The compound according to claim 1 wherein t is 0 or 1.

21. The compound according to claim 2 wherein t is 0 or 1.

22. The compound according to claim 10 wherein t is 0 or 1.

23. The compound according to claim 19 wherein t is 0 or 1.

24. The compound according to claim 1 wherein m is 2 and t is 1.

25. The compound according to claim 2 wherein m is 2 and t is 1.

26. The compound according to claim 10 wherein m is 2 and t is 1.

27. The compound according to claim 1 wherein R2 and R3 are both phenyl, R4 and R5 are both hydrogen, m is 2 and t is 1.

28. The compound according to claim 1 wherein R6 is hydrogen.

29. The compound according to claim 2 wherein R6 is hydrogen.

30. The compound according to claim 10 wherein R6 is hydrogen.

31. The compound according to claim 1 wherein F, G, H, K and L are independently selected from the group consisting of hydrogen, halogen, methyl and or methoxy.

32. The compound according to claim 2 wherein F, G, H, K and L are independently selected from the group consisting of hydrogen, halogen, methyl and or methoxy.

33. The compound according to claim 1 wherein p is 0.

34. The compound according to claim 2 wherein p is 0.

35. The compound according to claim 1 wherein R7 is hydrogen.

36. The compound according to claim 2 wherein R7 is hydrogen.

37. The pharmaceutically acceptable anion according to claim 1 which is bromide.

38. The pharmaceutically acceptable anion according to claim 1 which is iodide.

39. The pharmaceutically acceptable anion according to claim 2 which is bromide.

40. The pharmaceutically acceptable anion according to claim 2 which is iodide.

41. The compound according to claim 1 which is:

4-[hydroxy(diphenyl)methyl]-1-[2-(phenyloxy)ethyl]-1-azoniabicyclo [2.2.2]octane bromide;

4-[hydroxy(diphenyl)methyl]-1-[3-(phenyloxy)propyl]-1-azoniabicyclo[2.2.2]octane bromide;

4-[hydroxy(di-2-thienyl)methyl]-1-[2-(phenyloxy)ethyl]-1-azoniabicyclo[2.2.2]octane bromide;

4-[hydroxy(di-2-thienyl)methyl]-1-[3-(phenyloxy)propyl]-1-azoniabicyclo[2.2.2]octane bromide;

4-[hydroxy(diphenyl)methyl]-1-[4-(phenyloxy)butyl]-1-azoniabicyclo[2.2.2]octane bromide;

4-[hydroxy(diphenyl)methyl]-1-{4-[(phenylmethyl)oxy]butyl}-1-azoniabicyclo[2.2.2]octane bromide;

4-[hydroxy(diphenyl)methyl]-1-{3-[(phenylmethyl)oxy]propyl}-1-azoniabicyclo[2.2.2]octane bromide;

1-{2-[(2,4-dibromophenyl)oxy]ethyl}-4-[hydroxy(diphenyl)methyl]-1-azoniabicyclo[2.2.2]octane bromide;

4-[hydroxy(di-3-thienyl)methyl]-1-[2-(phenyloxy)ethyl]-1-azoniabicyclo[2.2.2]octane bromide;

4-[hydroxy(di-3-thienyl)methyl]-1-[3-(phenyloxy)propyl]-1-azoniabicyclo[2.2.2]octane bromide;

4-[hydroxy(diphenyl)methyl]-1-(3-{[2-(methyloxy)phenyl]oxy}propyl)-1-azoniabicyclo[2.2.2]octane bromide;

4-[hydroxy(diphenyl)methyl]-1-{3-[2-hydroxyphenyl)oxy]propyl}-1-azoniabicyclo[2.2.2]octane bromide;

1-{3-[(3-chlorophenyl)oxy]propyl}-4-[hydroxy(diphenyl)methyl]-1-azoniabicyclo[2.2.2]octane bromide;

1-{3-[(4-bromophenyl)oxy]propyl}-4-[hydroxy(diphenyl)methyl]-1-azoniabicyclo[2.2.2]octane bromide;

4-[hydroxy(diphenyl)methyl]-1-{3-[(4-nitrophenyl)oxy]propyl}-1-azoniabicyclo[2.2.2]octane bromide;

1-{3-[(2-bromophenyl)oxy]propyl}-4-[hydroxy(diphenyl)methyl]-1-azoniabicyclo[2.2.2]octane bromide;

4-[hydroxy(diphenyl)methyl]-1-(3-{[4-(methyloxy)phenyl]oxy}propyl)-1-azoniabicyclo[2.2.2]octane bromide;

4-[hydroxy(di-2-naphthalenyl)methyl]-1-[3-(phenyloxy)propyl]-1-azoniabicyclo[2.2.2]octane bromide;

4-[hydroxy(di-2-naphthalenyl)methyl]-1-{2-[(phenylmethyl)oxy]ethyl}-1-azoniabicyclo[2.2.2]octane bromide;

1-{3-[(2-fluorophenyl)oxy]propyl}-4-[hydroxy(diphenyl)methyl]-1-azoniabicyclo[2.2.2]octane bromide;

1-{3-[(3-fluorophenyl)oxy]propyl}-4-[hydroxy(diphenyl)methyl]-1-azoniabicyclo[2.2.2]octane bromide;

1-{3-[(4-fluorophenyl)oxy]propyl}-4-[hydroxy(diphenyl)methyl]-1-azoniabicyclo[2.2.2]octane bromide;

1-[3-(3-biphenylyloxy)propyl]-4-[hydroxy(diphenyl)methyl]-1-azoniabicyclo[2.2.2]octane bromide;

1-[3-(4-biphenylyloxy)propyl]-4-[hydroxy(diphenyl)methyl]-1-azoniabicyclo[2.2.2]octane bromide;

4-[hydroxy(diphenyl)methyl]-1-{3-[(3-nitrophenyl)oxy]propyl}-1-azoniabicyclo[2.2.2]octane bromide;

4-[hydroxy(diphenyl)methyl]-1-{3-[(2-methylphenyl)oxy]propyl}-1-azoniabicyclo[2.2.2]octane bromide;

1-(3-{[3-(diethylamino)phenyl]oxy}propyl)-4-[hydroxy(diphenyl)methyl]-1-azoniabicyclo[2.2.2]octane bromide;

4-[hydroxy(diphenyl)methyl]-1-[2-({[3-(methyloxy)phenyl]methyl}oxy)ethyl]-1-azoniabicyclo[2.2.2]octane bromide;

1-[2-({[4-(1,1-dimethylethyl)phenyl]methyl}oxy)ethyl]-4-[hydroxy(diphenyl)methyl]-1-azoniabicyclo[2.2.2]octane bromide;

1-(2-{[(4-fluorophenyl)methyl]oxy}ethyl)-4-[hydroxy(diphenyl)methyl]-1-azoniabicyclo[2.2.2]octane bromide;

1-(2-{[(4-chlorophenyl)methyl]oxy}ethyl)-4-[hydroxy(diphenyl)methyl]-1-azoniabicyclo[2.2.2]octane bromide;

1-(2-{[(4-bromophenyl)methyl]oxy}ethyl)-4-[hydroxy(diphenyl)methyl]-1-azoniabicyclo[2.2.2]octane bromide;

1-(2-{[(4-cyanophenyl)methyl]oxy}ethyl)-4-[hydroxy(diphenyl)methyl]-1-azoniabicyclo[2.2.2]octane bromide;

4-[hydroxy(diphenyl)methyl]-1-{2-[(2-naphthalenylmethyl)oxy]ethyl}-1-azoniabicyclo[2.2.2]octane bromide;

1-{3-[(4-cyanophenyl)oxy]propyl}-4-[hydroxy(diphenyl)methyl]-1-azoniabicyclo[2.2.2]octane bromide;

4-[hydroxy(diphenyl)methyl]-1-{2-[(1-methyl-1-phenylethyl)oxy]ethyl}-1-azoniabicyclo [2.2.2]octane bromide; or 1-(2-{[(3-fluorophenyl)methyl]oxy}ethyl)-4-[hydroxy(diphenyl)methyl]-1-azoniabicyclo[2.2.2]octane bromide.

42. The compound according to claim 1 which is:

4-[bis(4-fluorophenyl)(hydroxy)methyl]-1-[3-(phenyloxy)propyl]-1-azoniabicyclo[2.2.2]octane bromide;

4-[bis(4-fluorophenyl)(hydroxy)methyl]-1-{2-[(phenylmethyl)oxy]ethyl}-1-azoniabicyclo[2.2.2]octane bromide;

4-(hydroxy{bis[3-(methyloxy)phenyl]}methyl)-1-[3-(phenyloxy)propyl]-1-azoniabicyclo[2.2.2]octane bromide;

4-(hydroxy{bis[3-(methyloxy)phenyl]}methyl)-1-{2-[(phenylmethyl)oxy]ethyl}-1-azoniabicyclo[2.2.2]octane bromide;

4-(hydroxy{bis[4-(methyloxy)phenyl]}methyl)-1-[3-(phenyloxy)propyl]-1-azoniabicyclo[2.2.2]octane bromide;

4-(hydroxy{bis[4-(methyloxy)phenyl]}methyl)-1-{2-[(phenylmethyl)oxy]ethyl}-1-azoniabicyclo[2.2.2]octane bromide;

4-[bis(3-fluorophenyl)(hydroxy)methyl]-1-[3-(phenyloxy)propyl]-1-azoniabicyclo[2.2.2]octane bromide;

4-[bis(3-fluorophenyl)(hydroxy)methyl]-1-{2-[(phenylmethyl)oxy]ethyl}-1-azoniabicyclo[2.2.2]octane bromide;

4-{hydroxy[bis(3-methylphenyl)]methyl}-1-[3-(phenyloxy)propyl]-1-azoniabicyclo[2.2.2]octane bromide;

4-{hydroxy[bis(3-methylphenyl)]methyl}-1-{2-[(phenylmethyl)oxy]ethyl}-1-azoniabicyclo[2.2.2]octane bromide;

4-{hydroxy[bis(4-methylphenyl)]methyl}-1-[3-(phenyloxy)propyl]-1-azoniabicyclo[2.2.2]octane bromide; or 4-{hydroxy[bis(4-methylphenyl)]methyl}-1-{2-[(phenylmethyl)oxy]ethyl}-1-azoniabicyclo[2.2.2]octane bromide.

43. A pharmaceutical composition comprising a compound according to claim 41 and a pharmaceutically acceptable carrier thereof.

44. A pharmaceutical composition comprising a compound according to claim 42 and a pharmaceutically acceptable carrier thereof.

45. A pharmaceutical composition comprising a compound according to claim 42 and a pharmaceutically acceptable carrier thereof.

46. A pharmaceutical composition according to claim 3 in a form suitable for administration by oral or nasal inhalation.

47. A pharmaceutical composition according to claim 46 wherein the form is suitable for administration by inhalation via a medicament dispenser selected from a reservoir dry powder inhaler, a multi-dose dry powder inhaler, or a metered dose inhaler.

48. A pharmaceutical composition according to claim 3 which is a dry powder composition.

49. A pharmaceutical composition according to claim 3 wherein the pharmaceutically acceptable carrier is lactose.

* * * * *